US009918807B2

(12) United States Patent
Cosse

(10) Patent No.: US 9,918,807 B2
(45) Date of Patent: Mar. 20, 2018

(54) DEVICES, SYSTEMS, AND METHODS FOR ADJUSTING A PRESCRIPTION OF A PLURALITY OF ORTHODONTIC BRACKETS

(71) Applicant: Christopher C. Cosse, Shreveport, LA (US)

(72) Inventor: Christopher C. Cosse, Shreveport, LA (US)

(*) Notice: Subject to any disclaimer, the term of this patent is extended or adjusted under 35 U.S.C. 154(b) by 253 days.

(21) Appl. No.: 14/694,308

(22) Filed: Apr. 23, 2015

(65) Prior Publication Data
US 2015/0305831 A1 Oct. 29, 2015

Related U.S. Application Data

(60) Provisional application No. 61/984,661, filed on Apr. 25, 2014.

(51) Int. Cl.
*A61C 3/00* (2006.01)
*A61C 7/02* (2006.01)
*A61C 7/14* (2006.01)

(52) U.S. Cl.
CPC .............. *A61C 7/02* (2013.01); *A61C 7/146* (2013.01)

(58) Field of Classification Search
CPC .................................. A61C 7/02; A61C 7/146
USPC .................................................. 433/3–16, 24
See application file for complete search history.

(56) References Cited

U.S. PATENT DOCUMENTS

| 1,280,628 | A | 10/1918 | Angle |
| 1,821,171 | A | 9/1931 | Atkinson |
| 3,435,527 | A | 4/1969 | Kesling |
| 3,772,787 | A | 11/1973 | Hanson |
| 4,077,126 | A | 3/1978 | Pletcher |
| 4,144,642 | A | 3/1979 | Wallshein |
| 4,171,568 | A | 10/1979 | Förster |
| 4,197,642 | A | 4/1980 | Wallshein |
| 4,243,387 | A * | 1/1981 | Prins ........................ A61C 7/12 433/16 |
| 4,248,588 | A | 2/1981 | Hanson |
| 4,371,337 | A | 2/1983 | Pletcher |
| 4,419,078 | A | 12/1983 | Pletcher |
| 4,492,573 | A | 1/1985 | Hanson |
| 4,512,740 | A | 4/1985 | Kurz |

(Continued)

FOREIGN PATENT DOCUMENTS

WO  WO 2011141937 A1 * 11/2011 ............... A61C 7/14

*Primary Examiner* — Cris L Rodriguez
*Assistant Examiner* — Matthew Saunders
(74) *Attorney, Agent, or Firm* — DASCENZO Intellectual Property Law, P.C.

(57) ABSTRACT

Devices, systems, and methods for adjusting a prescription of a plurality of orthodontic brackets are disclosed herein. The devices include an orthodontic prescription-defining device that includes a plurality of contacting structures and a plurality of prescription-defining engagement structures. The systems include the orthodontic prescription-defining device and a plurality of orthodontic brackets. The methods include unlocking each of a plurality of orthodontic brackets, operatively contacting a plurality of contacting structures of an orthodontic prescription-defining device with a plurality of intra-oral reference points, urging each of a plurality of archwire slots to a respective preselected orientation, and locking each of the plurality of orthodontic brackets in the preselected orientation.

25 Claims, 8 Drawing Sheets

(56) References Cited

U.S. PATENT DOCUMENTS

| | | |
|---|---|---|
| 4,531,911 A | 7/1985 | Creekmore |
| 4,559,012 A | 12/1985 | Pletcher |
| 4,561,844 A | 12/1985 | Bates |
| 4,597,739 A | 7/1986 | Rosenberg |
| 4,614,497 A | 9/1986 | Kurz |
| 4,655,708 A | 4/1987 | Fujita |
| 4,698,017 A | 10/1987 | Hanson |
| 4,712,999 A | 12/1987 | Rosenberg |
| 4,878,840 A | 11/1989 | Reynolds |
| 4,913,654 A | 4/1990 | Morgan et al. |
| 5,037,296 A | 8/1991 | Karwoski |
| 5,094,614 A | 3/1992 | Wildman |
| 5,322,435 A | 6/1994 | Pletcher |
| 5,562,444 A | 10/1996 | Heiser et al. |
| 5,586,881 A | 12/1996 | Chikami |
| 5,711,666 A | 1/1998 | Hanson |
| 5,857,850 A | 1/1999 | Voudouris |
| 5,863,198 A | 1/1999 | Doyle |
| 5,868,787 A | 2/1999 | Kim |
| 5,954,500 A | 9/1999 | Spriggs |
| 6,193,508 B1 | 2/2001 | Georgakis |
| 6,302,688 B1 | 10/2001 | Jordan et al. |
| 6,358,045 B1 | 3/2002 | Farzin-Nia et al. |
| 6,447,291 B2 | 9/2002 | Kim |
| 6,554,613 B1 * | 4/2003 | Sachdeva ............ A61C 7/00 433/24 |
| 6,582,226 B2 | 6/2003 | Jordan et al. |
| 6,655,957 B2 | 12/2003 | Abels et al. |
| 6,659,766 B2 | 12/2003 | Abels et al. |
| 7,094,053 B2 | 8/2006 | Andreiko |
| 7,690,917 B2 | 4/2010 | Marshall |
| 7,740,475 B2 * | 6/2010 | Minium ............ A61C 7/14 433/16 |
| 7,845,940 B2 * | 12/2010 | Minium ............ A61C 7/04 433/10 |
| 8,337,198 B2 | 12/2012 | Cosse |
| 8,496,473 B2 | 7/2013 | Phan et al. |
| 8,539,955 B2 | 9/2013 | Foster |
| 2003/0224310 A1 * | 12/2003 | Andreiko ............ A61C 7/146 433/3 |
| 2007/0031775 A1 | 2/2007 | Andreiko |
| 2008/0090196 A1 | 4/2008 | Lomas |
| 2008/0293005 A1 | 11/2008 | Rahlis et al. |
| 2010/0190125 A1 | 7/2010 | Lee |
| 2011/0183280 A1 | 7/2011 | Cosse et al. |
| 2012/0148971 A1 | 6/2012 | Yamamoto et al. |
| 2012/0308952 A1 | 12/2012 | Cosse |
| 2013/0004910 A1 | 1/2013 | Halbich |
| 2013/0252193 A1 | 9/2013 | Bowman et al. |
| 2014/0251348 A1 | 9/2014 | Lemchen et al. |
| 2014/0255864 A1 * | 9/2014 | MacHata ............ A61C 7/146 433/3 |
| 2014/0272751 A1 * | 9/2014 | Cosse ............ A61C 7/02 433/9 |
| 2014/0335467 A1 | 11/2014 | Yamamoto et al. |
| 2014/0349241 A1 | 11/2014 | Okazaki |
| 2014/0363779 A1 | 12/2014 | Kopelman |

* cited by examiner

DEVICES, SYSTEMS, AND METHODS FOR ADJUSTING A PRESCRIPTION OF A PLURALITY OF ORTHODONTIC BRACKETS

RELATED APPLICATION

This application claims priority to U.S. Provisional Patent Application Ser. No. 61/984,661, which was filed on Apr. 25, 2014, and the complete disclosure of which is hereby incorporated by reference.

FIELD OF THE DISCLOSURE

The present disclosure is directed generally to devices, systems, and methods for adjusting a prescription of a plurality of orthodontic brackets, and more particularly to devices, systems, and methods that utilize an orthodontic prescription-defining device to concurrently adjust a relative orientation between an archwire slot and a base of each of the plurality of orthodontic brackets.

BACKGROUND OF THE DISCLOSURE

Orthodontic brackets typically are small, slotted devices for use during orthodontic treatment of a patient's teeth. The brackets usually are configured for attachment to the front surfaces of the teeth, either by directly cementing a bracket to a tooth surface or by bonding the bracket to a metal band that encircles the tooth, though in some instances brackets may be attached to the back surfaces of teeth. Slots in the brackets, which may be referred to herein as archwire slots and/or as archwire passages, are disposed horizontally, or generally horizontally, and are configured to receive an archwire. Traditionally, an archwire is a resilient, curved piece of wire that may be bent and/or twisted prior to installation in the bracket slots, with the archwire typically extending through the slots of all of the orthodontic brackets that are attached to a patient's upper or lower teeth. Engagement between the archwire and the brackets creates corrective, or prescriptive, forces that are directed to the teeth by the orthodontic brackets to urge the teeth into a correct, or desired, alignment, or occlusion.

Orthodontic treatment of a patient's teeth typically requires periodic adjustment of the forces that are imparted to the teeth by the installed orthodontic brackets, archwire(s), etc. Adjustments include changing the magnitude and/or direction of the forces that are imparted to the patient's teeth, such as to adjust the degree to which torque, tip, and/or rotational forces are imparted to the patient's teeth to change the angulation, inclination, rotation, height, and/or location of the teeth. This may move the teeth toward an optimal, or desired, occlusion.

As used herein, tipping forces refer to forces applied to a tooth in the mesial-distal direction. Thus, tipping forces may impact angulation. Torsional forces refer to forces applied to the tooth by an archwire that is in torsion within the archwire passage. Thus, torsional forces tend to rotate the tooth in the buccal-lingual or labial-lingual direction and may impact inclination. Rotational forces refer to applied forces that tend to rotate the tooth about its long axis.

Adjustment of these forces traditionally is a trial-and-error process that requires removal of the archwire from the archwire slot, bending of the archwire, and re-insertion of the archwire into the archwire slot. Alternatively, the archwire slot may be repositioned. This may include repositioning by removing one or more orthodontic brackets from the patient's teeth and re-locating (the same or a different) orthodontic brackets on the patient's teeth.

Some adjustable orthodontic brackets permit repositioning of the archwire slot without removal of the orthodontic bracket from the patient's tooth. However, this process still may be time-consuming and/or may require some amount of trial-and-error fitting. Additionally, adjustable brackets may pose challenges for accurately determining a current archwire slot position, such as with respect to a defined treatment plan, and/or the degree to which an adjustment in the archwire slot position accurately reaches a desired position, which also may be defined by the treatment plan.

Thus, there exists a need for improved devices, systems, and methods for adjusting a prescription of a plurality of orthodontic brackets.

SUMMARY OF THE DISCLOSURE

Devices, systems, and methods for adjusting a prescription of a plurality of orthodontic brackets are disclosed herein. The devices include an orthodontic prescription-defining device. The device is configured to concurrently adjust an orientation of a plurality of orthodontic brackets while each of the orthodontic brackets is operatively affixed to a corresponding tooth within a patient's mouth. Each of the orthodontic brackets includes a base, which is configured to be operatively affixed to a corresponding tooth, and a body, which is configured to be selectively repositioned relative to the base and defines an archwire slot that is configured to receive an archwire. Each of the orthodontic brackets defines a locked configuration and an unlocked configuration.

The device includes a plurality of contacting structures. Each of the contacting structures is configured to operatively contact a predetermined intra-oral reference point within the patient's mouth to define a predetermined orientation of the orthodontic prescription-defining device within the patient's mouth. The device also includes a plurality of prescription-defining engagement structures. Each of the prescription-defining engagement structures is configured to urge at least one archwire slot to a respective preselected orientation between the archwire slot and the plurality of intra-oral reference points. The systems include the orthodontic prescription-defining device and a plurality of orthodontic brackets.

The methods include methods of adjusting an orientation of a plurality of archwire slots of a plurality of orthodontic brackets to define a prescription of the plurality of orthodontic brackets. The methods are configured to be performed while the orthodontic brackets are operatively affixed to a corresponding plurality of teeth within a patient's mouth. The methods include unlocking each of the orthodontic brackets to be adjusted, by transitioning each of the orthodontic brackets to a corresponding unlocked configuration, and operatively contacting a plurality of contacting structures of an orthodontic prescription-defining device with a plurality of intra-oral reference points. The operatively contacting may define a predetermined orientation of the orthodontic prescription-defining device within a patient's mouth. Concurrently with the operatively contacting, the methods further include urging each of a plurality of archwire slots to a respective preselected orientation with a plurality of prescription-defining engagement structures of the orthodontic prescription-defining device. The methods also include locking each of the plurality of orthodontic brackets by transitioning each of the orthodontic brackets to a corresponding locked configuration.

DETAILED DESCRIPTION AND BEST MODE OF THE DISCLOSURE

Figure 1:
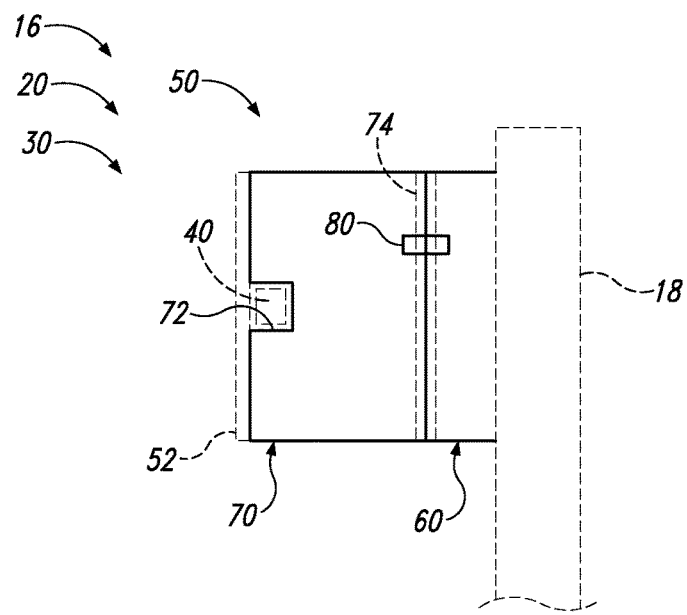
FIG. 1 is a schematic representation of examples of an adjustable orthodontic bracket.

FIGS. 1-17 provide examples of orthodontic appliance systems 20, of orthodontic prescription-defining devices 30, and/or of methods 100 according to the present disclosure. Elements that serve a similar, or at least substantially similar, purpose are labeled with like numbers in each of FIGS. 1-17, and these elements may not be discussed in detail herein with reference to each of FIGS. 1-17. Similarly, all elements may not be labeled in each of FIGS. 1-17, but reference numerals associated therewith may be utilized herein for consistency. Elements, components, and/or features that are discussed herein with reference to one or more of FIGS. 1-17 may be included in and/or utilized with any of FIGS. 1-17 without departing from the scope of the present disclosure.

In general, elements that are likely to be included in a given (i.e., a particular) embodiment are illustrated in solid lines, while elements that are optional to a given embodiment are illustrated in dashed lines. However, elements that are shown in solid lines are not essential to all embodiments, and an element shown in solid lines may be omitted from a given embodiment without departing from the scope of the present disclosure.

FIG. 1 is a schematic representation of examples of an adjustable orthodontic bracket 50 having an adjustable archwire passage, or archwire slot 72. Bracket 50 may form a portion of an orthodontic appliance system 20 according to the present disclosure. Bracket 50 includes a base 60, which is configured to be operatively attached to a tooth 18 that is present within a patient's mouth 16. It is within the scope of the present disclosure that bracket 50 may be operatively attached to any suitable surface of tooth 18, including a front (buccal/labial) surface of the tooth and/or a back (lingual) surface of the tooth. This operative attachment often will be directly to the surface of the tooth, although it is within the scope of the present disclosure that bracket 50 may be mounted on a band or other intermediate structure that is secured to the patient's tooth.

Bracket 50 also includes a body 70 that at least partially, if not completely, defines archwire slot 72, which is shaped to receive an archwire 40 during orthodontic treatment of a patient's teeth. Body 70 additionally or alternatively may be referred to herein as an archwire slot-defining body 70. Because body 70 contains and/or defines archwire slot 72 of the bracket, body 70 additionally or alternatively may be referred to as a corrective assembly 70, as the relative orientation of the body with respect to the patient's tooth to which the bracket is mounted affects the prescriptive forces that are imparted to the tooth during orthodontic treatment. Body 70 may be at least partially, if not completely, housed within base 60, although it also is within the scope of the present disclosure that at least a portion, or even all, of the body is external base 60.

Body 70 may be configured to be adjusted, or repositioned, relative to base 60 without detaching the body from the base and/or without detaching the base from the tooth. This relative adjustment of the orientation and/or position of the body relative to the base, such as to translate, rotate, and/or pivot the body relative to the base, results in a corresponding adjustment of archwire slot 72 relative to the base, and thereby relative to the patient's tooth to which the base is attached. Thus, relative adjustment of the body relative to the base changes the prescription that is defined by the bracket, and thus the forces that are imparted to the patient's teeth during prescriptive use of the bracket. As used herein, "prescriptive use" and/or "orthodontic use" refer to use of a bracket that is secured to a patient's tooth, and which contains an archwire operatively secured within the bracket's archwire slot, to apply forces to the patient's tooth to alter the relative orientation of the patient's tooth in the patient's mouth. Similarly, "operatively," when used herein to describe a relationship between two or more components or elements, refers to the functionality for which the components or elements are designed to be used, assembled, mounted, coupled, etc.

As schematically illustrated in FIG. 1, the adjustment of body, or corrective assembly, 70 relative to base 60 is enabled by an adjustment mechanism 74 that operatively couples the body to the base and permits selective adjustment of the body relative to the base. The adjustment mechanism may enable, or define, a single axis or plane of adjustment, such as by defining a pivot axis, a rotation axis, a translational direction (or axis), etc. of the body relative to the base. Alternatively, the adjustment mechanism may enable, or define, more than one degree of relative movement, such as to adjust two or more of the torque, the tip, and/or the rotation imparted to the patient's tooth during prescriptive use of the bracket. As examples, adjustment mechanism 74 may be configured to permit body 70 to rotate relative to base 60 about at least one rotational axis, about at least two rotational axes, or about three distinct rotational axes. As additional examples, adjustment mechanism 74 may be configured to permit body 70 to translate relative to base 60 along at least one translational axis, along at least two translational axes, or along three distinct translational axes.

These axes of rotational and/or translational motion between base 60 and body 70 may be referred to herein as degrees of freedom of body 70 relative to base 60. It is within the scope of the present disclosure that orthodontic bracket 50 may be configured such that body 70 has one, two, three, four, five, or six degrees of freedom relative to base 60 via any suitable combination of the above-described rotational and/or translational relative motions.

Structurally, adjustment mechanism 74 may define the permitted relative movement of body 70 relative to base 60. The adjustment mechanism may be a separate component that interconnects the base and the body. Alternatively, the adjustment mechanism may form at least a portion of the base and/or of the body, such as by having portions of the adjustment mechanism be part of the base and/or of the body. Examples of structures and/or mechanisms that may be utilized by adjustment mechanism 74 to provide the relative movement between the base and the body include one or more slides, pivots, races, hinges, ball-and-sockets, dovetail assemblies, springs, elastomers, compliant members, grooves, slides, sliders, rails, tracks, channels, ratchets, axles, wedges, etc.

As also schematically illustrated in FIG. 1, bracket 50 further may include a retention structure 80 that selectively secures body 70 in a selected orientation relative to base 60 (and thus relative to patient's tooth 18 to which the bracket is mounted). Retention structure 80 thus may be described as selectively restricting adjustment of the position of the body independent of and/or relative to the base of the bracket. The retention structure may take any suitable form and/or utilize any suitable structure, and the retention structure may be integrated with, cooperate with, and/or function independent of adjustment mechanism 74 without departing from the scope of the present disclosure.

Retention structure 80 is configured to be selectively transitioned between a locked configuration and an unlocked configuration. In the locked configuration, retention structure 80 restricts relative movement between body 70 and base 60 of bracket 50, thereby restricting adjustment of the position of archwire slot 72 relative to patient's tooth 18 to which the bracket is attached. In the unlocked configuration, retention structure 80 permits the body to be moved relative to, or independent of, the base of the bracket, such as responsive to engagement by an orthodontic prescription-defining device 30, as discussed in more detail herein with reference to FIGS. 2-17. However, when in the unlocked configuration, retention structure 80 still may resist separation of body 70 from base 60 and/or may operatively attach, or couple, body 70 to base 60. The locked configuration additionally or alternatively may be referred to herein as a secured configuration, a tightened configuration, and/or an operative configuration. The unlocked configuration additionally or alternatively may be referred to herein as an adjustment configuration, a loosened configuration, and/or a released configuration. When the retention structure is in the locked or unlocked configuration, the orthodontic bracket additionally or alternatively may be referred to herein as being in the locked or unlocked configuration.

Retention structure 80 may include any suitable structure that is configured to transition between the locked configuration and the unlocked configuration, that is configured to selectively maintain the orientation of archwire slot 72 relative to base 60, that is configured to selectively permit the orientation of the archwire slot to be varied, and/or that is configured to (at least selectively) retain the body operatively attached to the base. As examples, retention structure 80 may include and/or be any suitable pin, latch, clasp, wedge, cam, fastener, etc.

Bracket 50 further may include at least one ligature 52 that is configured to retain archwire 40 within archwire slot 72. Ligature 52 may include any suitable structure that may, or that may be utilized to, retain archwire 40 within archwire slot 72. This may include any suitable ligating structure that is configured to be operatively attached and/or affixed to base 60 and/or to body 70, such as an elastomeric band, as well as any suitable ligating structure that forms a portion of bracket 50, such as when bracket 50 is a self-ligating bracket 50.

Orthodontic bracket 50, which is schematically illustrated in FIG. 1, may have any suitable shape, size, and/or components for receiving archwire 40 into archwire slot 72 of the bracket to impart prescriptive forces to tooth 18 during orthodontic use of the bracket. As discussed, bracket 50 is an adjustable orthodontic bracket 50 and may include any suitable orthodontic bracket that is adapted, configured, designed, and/or constructed to permit adjustment of the orientation of archwire slot 72 relative to a reference orientation thereof, relative to base 60, relative to tooth 18, relative to another tooth that may be present within patient's mouth 16, and/or relative to another orthodontic bracket that may be present within patient's mouth 16. Additionally or alternatively, this also may include any suitable orthodontic bracket that may be configured to permit adjustment of the orientation of the archwire slot while the bracket is operatively attached to the tooth and/or without separation of the bracket from the tooth.

Bracket 50 also may, but is not required to, include additional components, regions, and/or features that are conventional to orthodontic bracket bases/bodies/housings, such as appropriately shaped and/or contoured tooth-contacting surfaces, tie wings, or other suitable mounts for ligating structures, such as ligatures, orthodontic chains, powerchains, springs, elastic bands, and the like. In this regard, examples of orthodontic brackets and bracket assemblies, as well as components and uses thereof, and accessories therefor, are disclosed in U.S. Pat. No. 8,337,198, in U.S. Patent Application Publication Nos. 2014/0272751, 2012/0308952 and 2011/0183280, in U.S. Provisional Patent Application No. 61/913,122, and in U.S. patent application Ser. No. 14/559,100, the complete disclosures of which are hereby incorporated by reference. These and the subsequently incorporated patent references additionally or alternatively disclose optional additional structures, features, components, and the like that may be used with bracket 50 (so long as doing so does not impair the operation and functionality expressly presented herein).

Additional examples of ligating orthodontic brackets are disclosed in U.S. Pat. Nos. 6,302,688, 6,582,226, 4,597,739, 4,878,840, 3,772,787, 4,248,588, 4,492,573, 4,614,497, 4,698,017, 1,280,628, 1,821,171, and 3,435,527, the disclosures of which are hereby incorporated by reference. Examples of self-ligating orthodontic brackets are disclosed in U.S. Pat. Nos. 6,659,766, 6,655,957, 6,358,045, 6,193,508, 5,857,850, 5,711,666, 5,562,444, 5,322,435, 5,094,614, 4,559,012, 4,531,911, 4,492,573, 4,419,078, 4,371,337, 4,077,126, 4,144,642, 4,248,588, 4,698,017, 3,772,787, 4,561,844, 4,655,708, 4,197,642, 4,712,999, and 4,171,568, the disclosures of which are hereby incorporated by reference. Still further additional examples of orthodontic brackets are disclosed in U.S. Pat. Nos. 7,819,660, 7,771,640, and 6,632,088, the disclosures of which are hereby incorporated by reference. The structures, features, applications, and methods of the above-identified references may be utilized with and/or incorporated into bracket 50 according to the present disclosure to the extent that doing so does not conflict with the express provisions of the present disclosure.

Figure 2:
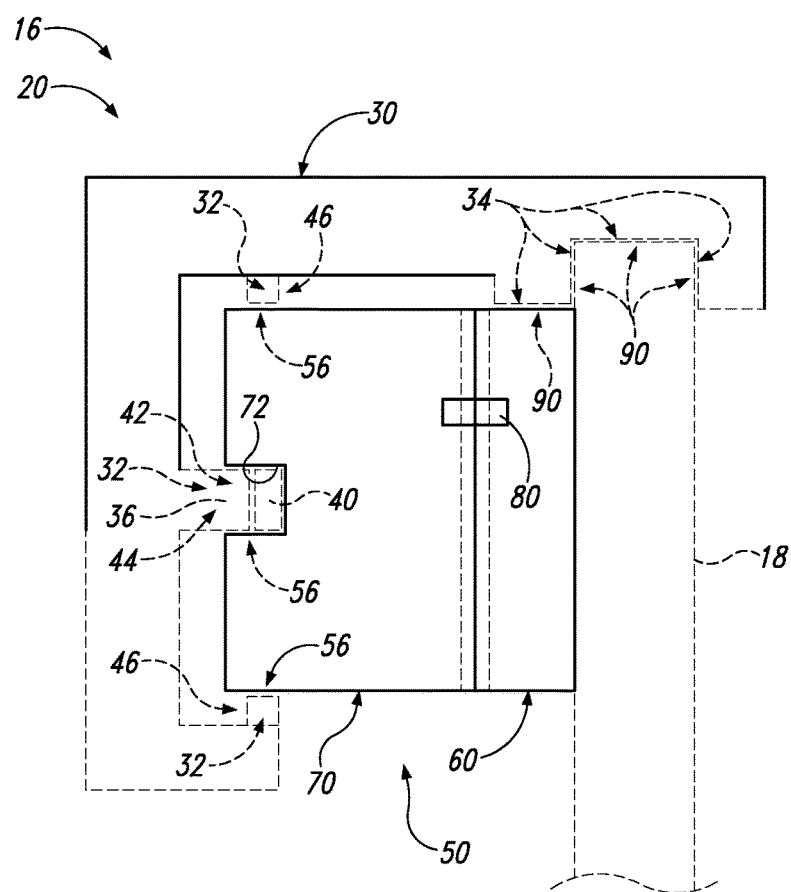
FIG. 2 is a schematic cross-sectional view of examples of an orthodontic appliance system that includes an adjustable orthodontic bracket and an orthodontic prescription-defining device according to the present disclosure.

FIG. 2 is a schematic cross-sectional view of examples of an orthodontic prescription-defining device 30 that may form a portion of an orthodontic appliance system 20 according to the present disclosure. Orthodontic prescription-defining device 30 also may be referred to herein as a device 30. Orthodontic appliance system 20 includes at least one orthodontic prescription-defining device 30 and at least one adjustable orthodontic bracket 50. Orthodontic appliance system 20 may include a plurality of adjustable orthodontic brackets 50 that is configured to be concurrently, or at least substantially concurrently, adjusted, such as to a predetermined or preselected orientation (prescription), by device 30.

As used herein, concurrent adjustment of a plurality of orthodontic brackets by orthodontic prescription-defining device 30 is intended to indicate that the orthodontic prescription-defining device is operatively engaged with every orthodontic bracket in the plurality of orthodontic brackets during an engagement timeframe and without removing the device from the patient's mouth and/or from the position defined by the plurality of intra-oral reference points that are discussed in more detail herein. Additionally or alternatively, concurrent adjustment also is intended to indicate that the orthodontic prescription-defining device urges each orthodontic bracket in the plurality of orthodontic brackets toward a respective preselected orientation during the engagement timeframe. Additionally or alternatively, concurrent adjustment also is intended to indicate that the orthodontic prescription-defining device retains each orthodontic bracket in the plurality of orthodontic brackets in the respective preselected orientation during the engagement timeframe.

It is within the scope of the present disclosure that the orthodontic prescription-defining device may simultaneously and/or concurrently initiate engagement with, adjustment of, and/or retention of each orthodontic bracket in the plurality of orthodontic brackets. Alternatively, it is also within the scope of the present disclosure that the orthodontic prescription-defining device may sequentially, consecutively, and/or successively initiate engagement with, adjustment of, and/or retention of each orthodontic bracket in the plurality of orthodontic brackets.

As discussed, orthodontic bracket 50 may include a base 60, a body 70, and a retention structure 80. As also discussed, body 70 may define an archwire slot 72 that may be sized to receive an archwire 40.

Device 30 includes a plurality of contacting structures 34 that may be adapted, shaped, constructed, and/or configured to operatively contact a corresponding plurality of intra-oral reference points 90 within a patient's mouth 16. This operative contact may operatively align and/or locate the orthodontic prescription-defining device, such as to define a predetermined orientation of the orthodontic prescription-defining device within the patient's mouth.

The plurality of contacting structures 34 may include any suitable number of contacting structures. As examples, the plurality of contacting structures may include at least 2, at least 3, at least 4, at least 5, at least 6, at least 8, at least 10, at least 12, or at least 14 contacting structures 34. The plurality of contacting structures may be spaced apart on the device or may collectively define a larger contacting structure that contacts the plurality of intra-oral reference points, such as portions of a series of adjacent teeth within the patient's mouth.

Examples of intra-oral reference point 90 include a portion of a tooth 18 to which bracket 50 is operatively affixed, an occlusal surface of tooth 18, a cusp tip of tooth 18, a portion of another tooth (other than tooth 18) that is in patient's mouth 16, an occlusal surface of the other tooth, a cusp tip of the other tooth, base 60, another bracket (other than the particular orthodontic bracket 50 whose body 70 and archwire slot 72 are being adjusted) that is present within the patient's mouth, and/or a base of the other bracket. Intra-oral reference point 90 additionally or alternatively may be referred to as an intra-oral reference 90, an intra-oral support 90, an intra-oral reference structure 90, and/or an intra-oral guide 90.

Device 30 also includes a plurality of prescription-defining engagement structures 32, at least one of which is illustrated in FIG. 2. Prescription-defining engagement structures 32 also may be referred to herein as engagement structures 32 and may be configured to define a preselected orientation between archwire slot 72 and intra-oral reference points 90 and/or between archwire slot 72 and base 60 of bracket 50. Engagement structures 32 may be configured to press, direct, and/or otherwise urge archwire slot 72 to a desired, predetermined, and/or preselected orientation relative to device 30, relative to intra-oral reference point 90, relative to base 60, and/or relative to tooth 18. This orientation may define a desired, predetermined, and/or preselected prescriptive force that may be applied to tooth 18 via archwire 40 when the archwire is located within the archwire slot. Engagement structures 32 may be configured to define and/or specify the orientation of archwire slot 72 in at least 1, at least 2, at least 3, at least 4, at least 5, or at least 6 degrees of freedom of body 70 relative to base 60.

The plurality of engagement structures 32 may include any suitable number of engagement structures. As examples, the plurality of engagement structures may include at least 2, at least 3, at least 4, at least 5, at least 6, at least 8, at least 10, at least 12, or at least 14 engagement structures 32.

As discussed in more detail herein, orthodontic bracket 50 may be transitioned to an unlocked configuration in which an orientation of archwire slot 72 relative to base 60 may be varied via relative motion between body 70 and base 60. Subsequently, a respective engagement structure 32 of device 30 may be utilized to urge archwire slot 72 to the preselected orientation. As discussed in more detail herein, orthodontic prescription-defining device 30 may operatively and simultaneously engage the bodies and/or archwire slots of a plurality of adjustable orthodontic brackets to simultaneously adjust the relative orientation of the corresponding archwire slots.

It is within the scope of the present disclosure that engagement structures 32 may urge archwire slot 72 to the preselected orientation in any suitable manner. As an example, engagement structure 32 may be configured to operatively engage with a reference structure 56 of orthodontic bracket 50.

As a more specific example, and as illustrated in FIG. 2 at 42, engagement structure 32 may be at least partially received within archwire slot 72, with archwire slot 72 functioning as reference structure 56. Such an engagement structure also may be referred to herein as a protrusion 36 that is sized to be received within the archwire slot. This may include being received within the archwire slot while archwire 40 also is present therein and/or being received within the archwire slot subsequent to removal of the archwire from the archwire slot and/or prior to receipt of the archwire into the archwire slot. Under these conditions, device 30 may be referred to herein as directly and operatively engaging the archwire slot to urge the archwire slot to the predetermined orientation.

As another example, and as indicated in FIG. 2 at 46, engagement structure 32 may be configured to operatively engage with at least one reference structure 56 that is spaced-apart from the archwire slot. Under these conditions, device 30 may be referred to herein as directly and operatively engaging the reference structure to urge the archwire slot to the predetermined orientation.

Additionally or alternatively, and as indicated in FIG. 2 at 44, engagement structure 32 may be configured to operatively engage with archwire 40 while archwire 40 extends within archwire slot 72. This may include operative engagement with a portion of the archwire that extends within the archwire slot and/or operative engagement with a portion of the archwire that is external to the archwire slot. Under these conditions, device 30 may be referred to herein as directly and operatively engaging archwire 40 to indirectly urge the archwire slot to the predetermined orientation.

Orthodontic prescription-defining device 30 may be formed in any suitable manner and/or based upon any suitable criteria. As an example, orthodontic prescription-defining device 30 may be formed by an orthodontic prescription-defining device fabrication assembly. Examples of the orthodontic prescription-defining device fabrication assembly include any suitable machine tool, mill, mold, electrical discharge machine, and/or three-dimensional printer. It is within the scope of the present disclosure that the orthodontic prescription-defining device fabrication assembly may be adapted, configured, sized, and/or constructed to be operated by an orthodontist and/or to be located and/or utilized within the orthodontist's office.

Device 30 may include and/or be a monolithic orthodontic prescription-defining device 30 that defines the plurality of contacting structures 34 and the plurality of engagement structures 32. Alternatively, device 30 also may include and/or be a composite prescription-defining device 30 that includes a contacting body that defines the plurality of contacting structures and that is operatively attached to the plurality of engagement structures, as discussed in more detail herein. When device 30 is the composite prescription-defining device 30, each of the plurality of engagement structures may be configured to be selectively transitioned between a disengaged configuration and an engaged configuration, as also discussed in more detail herein.

A shape of orthodontic prescription-defining device 30, or at least a location and/or orientation of engagement structure 32 and/or contacting structure 34, may be selected based upon any suitable criteria. As examples, the shape of orthodontic prescription-defining device 30 may be based upon a three-dimensional (digital or physical) model of tooth 18, based upon a three-dimensional (digital or physical) model of a location of tooth 18 relative to at least one other tooth of the patient, an initial occlusion of tooth 18, a current (or present) occlusion of tooth 18, a desired occlusion for tooth 18, and/or a location of orthodontic bracket 50 on tooth 18. As additional examples, a predetermined treatment plan, measured and/or calculated data regarding the orientation of the tooth and/or prior/desired movement of the tooth, and/or prior and/or current images of the tooth may be utilized to select the shape of orthodontic prescription-defining device 30, or at least a location and/or orientation of engagement structures 32 and/or of contacting structures 34.

As discussed, orthodontic prescription-defining device 30 may be shaped to define a preselected relative orientation between archwire slot 72 and base 60 of orthodontic bracket 50. This preselected relative orientation may be inherent to a shape of orthodontic prescription-defining device 30 and/or may be fixed, or constant, for a given orthodontic prescription-defining device 30. As such, and in contrast to an adjustment tool that might be utilized to select a desired relative orientation between archwire slot 72 and base 60 from a plurality of potential relative orientations, the preselected relative orientation between the archwire slot and the base is defined by orthodontic prescription-defining device 30 according to the present disclosure. The preselected relative orientation may be fixed for a given orthodontic prescription-defining device 30, may be fixed and/or defined prior to contact between the orthodontic prescription-defining device and the intra-oral reference point, and/or may be fixed prior to contact between the orthodontic prescription-defining device and the orthodontic bracket, and/or may be fixed prior to contact between the orthodontic prescription-defining device and the archwire.

For simplicity, FIG. 2 illustrates orthodontic prescription-defining device 30 as urging the archwire slot of a single orthodontic bracket 50. However, as discussed, patient's mouth 16 will include a plurality of teeth 18 and a plurality of corresponding orthodontic brackets 50 may be operatively affixed to the teeth. Under these conditions, orthodontic prescription-defining device 30 may be adapted, shaped, designed, sized, constructed, and/or configured to concurrently contact (at least a portion of) the plurality of orthodontic brackets and one or more intra-oral reference points when each of the plurality of orthodontic brackets is in a respective unlocked configuration. In addition, orthodontic prescription-defining device 30 also may be adapted, shaped, designed, sized, constructed, and/or configured to adjust a respective archwire slot of each of the plurality of orthodontic brackets to define a respective preselected orientation between the respective archwire slot and a remainder of the orthodontic brackets and/or between the respective archwire slot and a respective base of a respective orthodontic bracket that defines the archwire slot. This may include adjusting the respective archwire slot of each orthodontic bracket with a single device 30 and/or utilizing a plurality of devices 30, wherein each of the plurality of devices 30 is configured to adjust a respective subset (but still at least two) of the plurality of archwire slots that corresponds to a respective subset of the plurality of orthodontic brackets.

Figure 3:
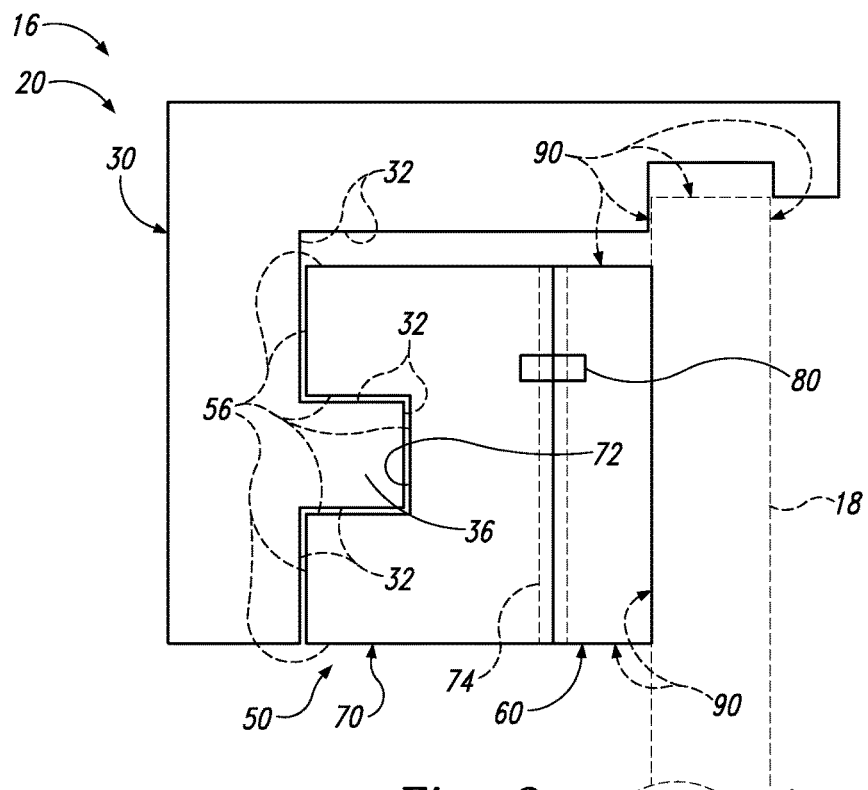
FIG. 3 is a schematic cross-sectional view of examples of an orthodontic appliance system that includes an adjustable orthodontic bracket and an orthodontic prescription-defining device according to the present disclosure.
Figure 4:
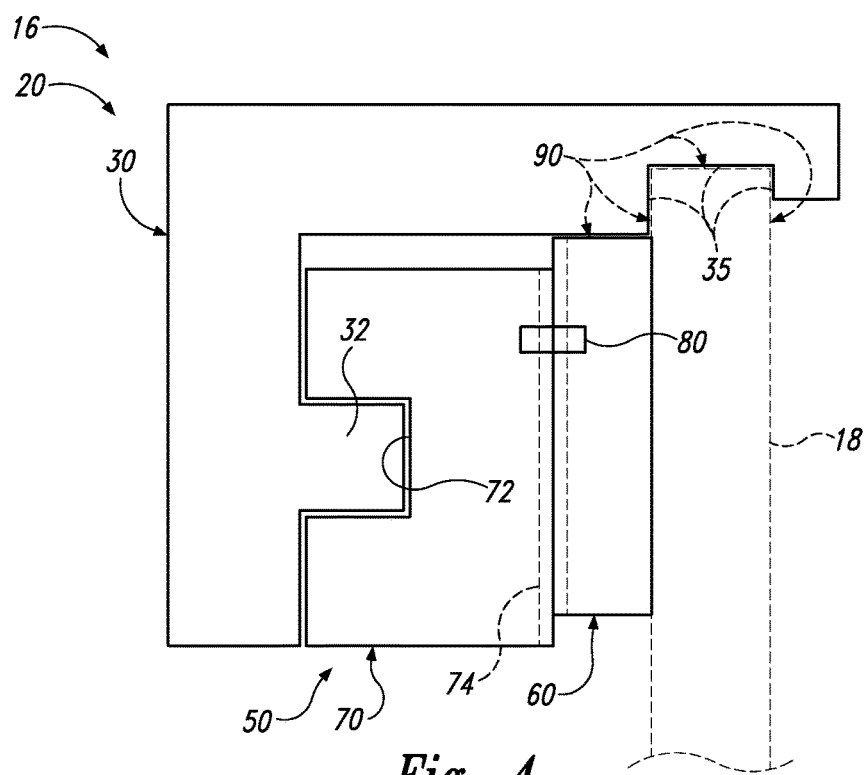
FIG. 4 is a schematic cross-sectional view of examples of an orthodontic appliance system that includes an adjustable orthodontic bracket and an orthodontic prescription-defining device according to the present disclosure.

FIGS. 3-4 schematically illustrate adjustment of archwire slot 72 via direct operative engagement between engagement structure 32 and the archwire slot. As illustrated in FIG. 3, body 70 (and thus archwire slot 72) initially may define and/or have a first, or given, relative orientation with respect to base 60. In FIG. 3, orthodontic prescription-defining device 30 is shown operatively engaging body 70 of bracket 50, but not intra-oral reference point(s) 90. Subsequently, and as shown in FIG. 4, orthodontic prescription-defining device 30 may be brought into contact with intra-oral reference point(s) 90 while also being operatively engaged with orthodontic bracket 50 while the orthodontic bracket is in the unlocked configuration. As a result of this dual contact/engagement, the relative orientation of body 70 and/or archwire slot 72 is adjusted relative to base 60, such as to a second (adjusted) orientation, which may be a preselected relative orientation that produces a desired corrective force on a tooth 18 to which orthodontic bracket 50 is affixed when an archwire is present within archwire slot 72. Thus, orthodontic prescription-defining device 30 may be utilized to accurately and/or efficiently align archwire slot 72 and base 60 to the preselected relative orientation. Subsequently, retention structure 80 may be transitioned to the locked configuration, thereby (at least substantially) fixing archwire slot 72 and base 60 in the preselected relative orientation. Then, orthodontic prescription-defining device 30 may be separated and/or disengaged from orthodontic bracket 50 and from intra-oral reference point 90. Although only a single tooth 18 and bracket 50 are shown in FIGS. 3-4 (and subsequently discussed FIGS. 8 and 13-14), orthodontic prescription-defining devices 30 will simultaneously engage a plurality of intra-oral reference points to concurrently adjust the orientations, and thus the prescriptions, of the archwire slots of a plurality of brackets 50.

It is within the scope of the present disclosure that this adjustment may occur with an archwire 40 removed from the archwire slot, as illustrated. Alternatively, orthodontic prescription-defining device 30 may be configured (i.e., shaped/sized) to provide the engagement and adjustment without first requiring removal of the archwire from the bracket's archwire slot.

It is within the scope of the present disclosure that orthodontic appliance system 20 may include a plurality of, or a plurality of different, orthodontic prescription-defining devices 30, with each orthodontic prescription-defining device 30 being adapted, shaped, designed, constructed, and/or configured to define a respective, or different, preselected relative orientation between archwire slot 72 and base 60 of a plurality of brackets 50. As an example, a first orthodontic prescription-defining device may be utilized to define a first relative orientation between the archwire slot and the base of a plurality of orthodontic brackets 50. An archwire then may be located within the archwire slot to define a first prescriptive force on the tooth for a first treatment time. Subsequently, a second orthodontic prescription-defining device may be utilized to define a second (different) relative orientation between the archwire slot and the base of the plurality of orthodontic brackets. An archwire (the same archwire or a different archwire) may be located within the archwire slot to define a second prescriptive force on the teeth for a second treatment time.

This process may be repeated any suitable number of times utilizing any suitable number of different orthodontic prescription-defining devices 30 that define any suitable number of different relative orientations between archwire slot 72 and base 60 (and thus any suitable number of different prescriptive forces). Within the context of an overall orthodontic treatment plan, such an orthodontic appliance system may be utilized to progressively, sequentially, and/or systematically vary the prescriptive forces that are applied to the patient's teeth. Such progressive variation in prescriptive forces also may be referred to herein as a progressive prescription sequence and may be utilized to move teeth 18 from an initial occlusion to a desired, or final, occlusion that may be different from the initial occlusion.

Figure 5:
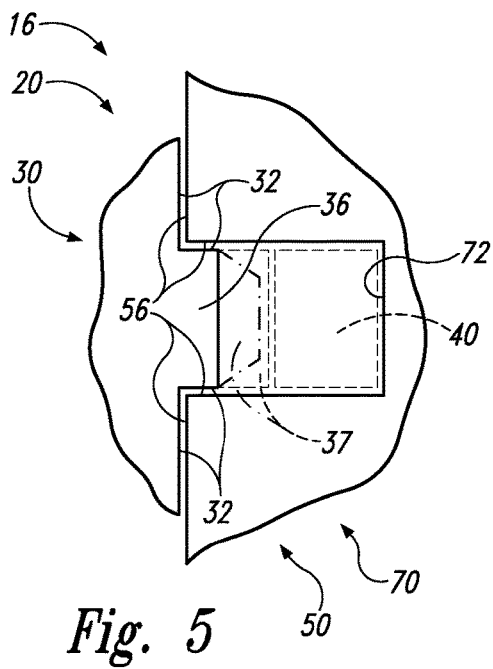
FIG. 5 is a fragmentary schematic cross-sectional view of a portion of an orthodontic prescription-defining device and a portion of a body of an adjustable orthodontic bracket according to the present disclosure.

It is within the scope of the present disclosure that the orthodontic prescription-defining device 30 and/or one or more engagement structures 32 thereof may include a guide structure 37 that facilitates alignment and/or operative engagement of the orthodontic prescription-defining device 30 with the body 70 of an orthodontic bracket 50. Examples of such guide structures 37 include compliant regions, tapered regions, flared regions, magnetic regions, etc. FIG. 5 schematically illustrates an engagement structure in the form of a protrusion 36 that is sized to be received into archwire slot 72 of body 70 of bracket 50. FIG. 5 graphically, albeit somewhat schematically, illustrates in dashed lines a guide structure 37 in the form of a compliant and/or resilient contact region that buffers the initial engagement of the engagement structure 32 of the device with reference structure 56 of the body. This buffering may ease and/or facilitate operative engagement of the engagement structure with the reference structure, especially when device 30 is used to operatively engage the bodies of a plurality of brackets simultaneously.

In dash-dot lines in FIG. 5, a guide structure 37 in the form of a tapered region is shown. Such a tapered region also may ease or facilitate operative engagement of the engagement structure with the reference structure, especially when device 30 is used to operatively engage the bodies of a plurality of brackets concurrently and/or simultaneously. In a further variant, the engagement structure may include a tapered and compliant/resilient region. FIG. 5 also provides a graphical example of an orthodontic prescription-defining device 30 operatively engaging the body of an orthodontic bracket while an archwire 40 is present within the archwire slot 72 of the body.

Figure 6:
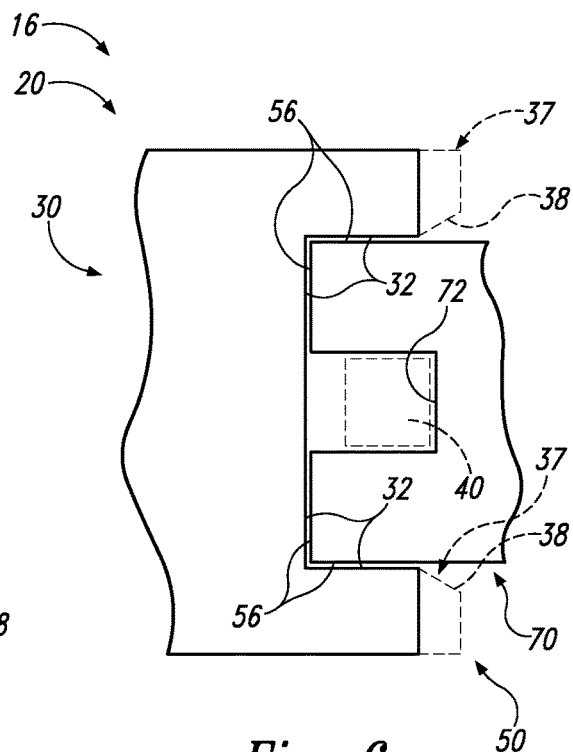
FIG. 6 is a fragmentary schematic cross-sectional view of a portion of an orthodontic prescription-defining device and a portion of a body of an adjustable orthodontic bracket according to the present disclosure.

FIG. 6 provides an example of an engagement structure 32 that is configured to operatively engage the sides and/or perimeter of body 70, with the sides of the body forming reference structure 56. The example of FIG. 6 also includes optional guide structure 37 in the form of flared regions 38 that assist in aligning the engagement structure for operative engagement with the reference structure. FIG. 6 also provides a further example of this operative engagement occurring without requiring removal of archwire 40 from archwire slot 72.

Figure 7:
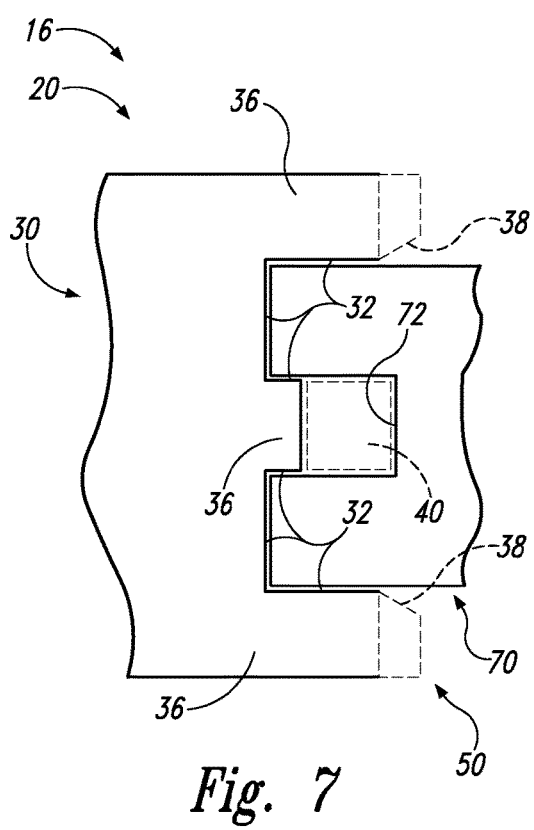
FIG. 7 is a fragmentary schematic cross-sectional view of a portion of an orthodontic prescription-defining device and a portion of a body of an adjustable orthodontic bracket according to the present disclosure.

FIG. 7 provides an example of an orthodontic prescription-defining device 30 with engagement structure 32 in the form of protrusion 36 and also engagement structures 32 that engage the sides, or outer perimeter, of the body. FIG. 7 also illustrates flared regions 38.

Figure 8:
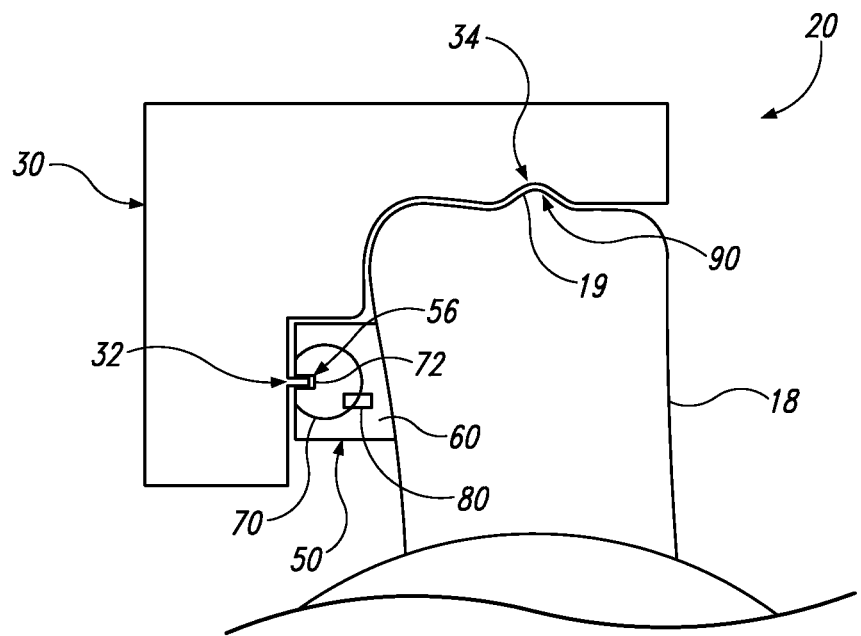
FIG. 8 is a less schematic cross-sectional view of another example of an orthodontic appliance system according to the present disclosure.

FIG. 8 is a less schematic cross-sectional view of another example of an orthodontic appliance system 20 according to the present disclosure. In FIG. 8, orthodontic appliance system 20 includes an orthodontic prescription-defining device 30. As illustrated, orthodontic prescription-defining device 30 includes an engagement structure 32 that is configured to be engaged within a reference structure 56 of an orthodontic bracket 50. In the example of FIG. 8, reference structure 56 includes and/or is an archwire slot 72 of orthodontic bracket 50. As further illustrated, orthodontic prescription-defining device 30 also includes a contacting structure 34. Contacting structure 34 is configured to contact an intra-oral reference point 90. In the example of FIG. 8, intra-oral reference point 90 includes and/or is a cusp tip 19 of a tooth 18.

As discussed in more detail herein, a spatial relationship and/or relative orientation between engagement structure 32 and contacting structure 34 is selected based upon a predetermined, or desired, relative orientation between archwire slot 72 and a base 60 of orthodontic bracket 50. Thus, operative engagement of orthodontic prescription-defining device 30 with orthodontic bracket 50, together with operative contact between contacting structure 34 and intra-oral reference point 90, produces the pre-determined relative orientation between archwire slot 72 and base 60. This orientation, in turn, configures the bracket to impart the preselected, or desired, prescriptive forces to the patient's tooth during orthodontic use of the bracket.

Figure 9:
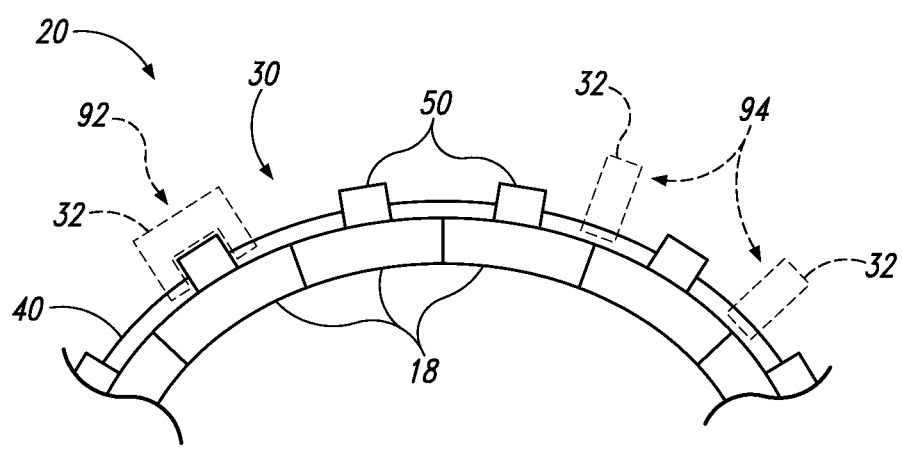
FIG. 9 is a schematic representation of examples of an orthodontic appliance system according to the present disclosure, as viewed from the gingival direction and illustrating engagement between a plurality of prescription-defining engagement structures and an archwire.

As discussed, device 30 additionally or alternatively may operatively engage an archwire 40 to urge one or more archwire slots to a respective preselected orientation between the one or more archwire slots and one or more intra-oral reference points. This is illustrated in FIG. 9. Therein, engagement structures 32 are illustrated as directly and operatively engaging archwire 40. It is within the scope of the present disclosure that the engagement between engagement structures 32 and archwire 40 may occur in any suitable manner.

As an example, and as indicated in FIG. 9 at 92, a single engagement structure 32 may be configured to span a given orthodontic bracket 50 and operatively engage archwire 40 on each side of orthodontic bracket 50. Such a configuration may permit precise and/or focused adjustment of an archwire slot that is associated with the spanned bracket 50.

As another example, and as indicated in FIG. 9 at 94, engagement structures 32 may operatively engage archwire 40 at a point that is between two adjacent orthodontic brackets 50. Such a configuration may permit a single engagement structure 32 to adjust both of the adjacent orthodontic brackets 50 and/or may provide an averaging effect in the adjustment between the adjacent orthodontic brackets.

Figure 10:
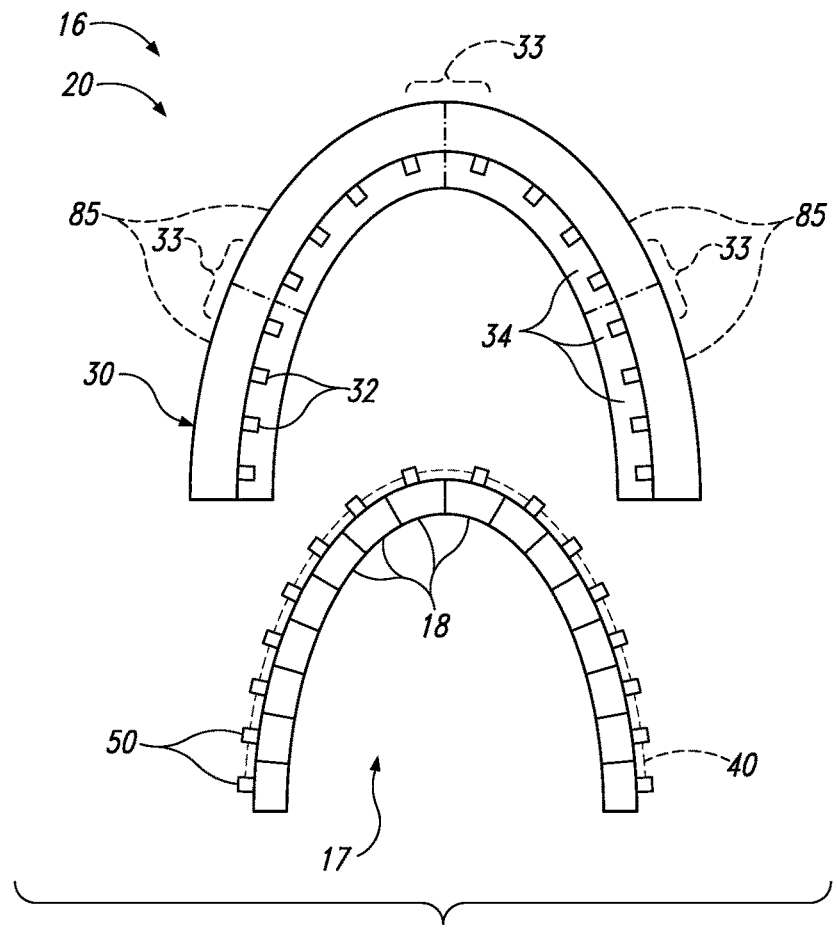
FIG. 10 is a schematic representation of examples of an orthodontic appliance system according to the present disclosure, as viewed from the gingival direction and with an orthodontic prescription-defining device disengaged from a plurality of orthodontic brackets.
Figure 11:
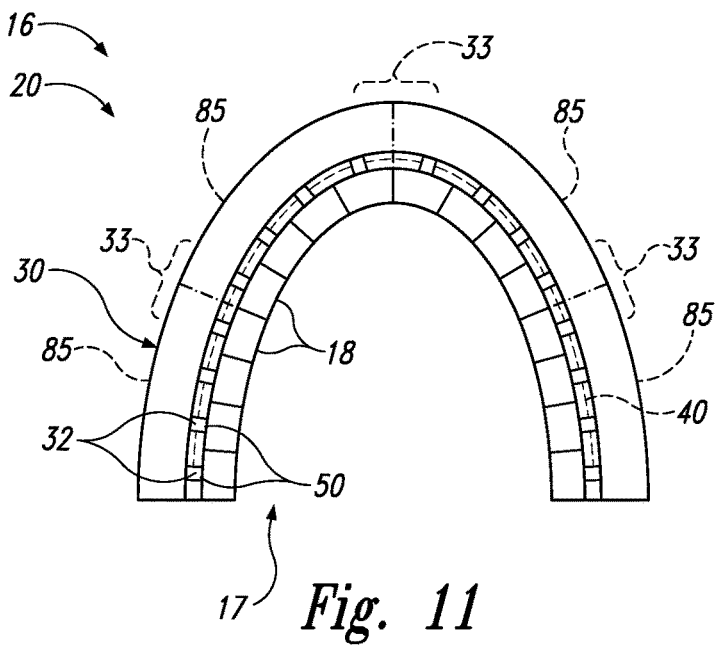
FIG. 11 is a schematic representation of the orthodontic appliance system of FIG. 10 with the orthodontic prescription-defining device operatively contacting a plurality of intra-oral reference points and operatively engaged with a plurality of orthodontic brackets.

FIGS. 10 and 11 are schematic representations of examples of an orthodontic appliance system 20 according to the present disclosure as viewed from the gingival direction. In FIGS. 10 and 11, a plurality of teeth 18, which may be present within a patient's mouth 16, have a plurality of respective orthodontic brackets 50 operatively affixed thereto. As illustrated in dashed lines, an archwire 40 may extend between orthodontic brackets 50; however, it is also within the scope of the present disclosure that the archwire may be removed. System 20 includes an orthodontic prescription-defining device 30. Orthodontic prescription-defining device 30 includes a plurality of engagement structures 32 that are configured to operatively engage respective orthodontic brackets 50 and/or archwire 40. Orthodontic prescription-defining device 30 also includes a plurality of contacting structures 34, which is configured to operatively contact an occlusal surface of one or more teeth 18. In FIGS. 10-11 device 30 may include a single and/or monolithic structure that defines engagement structures 32 and contacting structures 34.

Orthodontic prescription-defining device 30 may include and/or be a single-piece (or single-component) orthodontic prescription-defining device 30 that may be configured to operatively contact all teeth 18 in a given dental arch 17 and/or to operatively engage all orthodontic brackets 50 that may be operatively affixed thereto. Additionally or alternatively, and as illustrated in dash-dot lines in FIGS. 10 and 11, orthodontic prescription-defining device 30 also may include one or more pieces, or components, with each piece being sized and/or configured to contact a selected portion of the teeth within the given dental arch and/or to operatively engage a selected portion of the orthodontic brackets that are operatively affixed to the teeth.

It is further within the scope of the present disclosure that an orthodontic prescription-defining device 30 that is comprised of a plurality of independently positionable pieces, or segments, 85 may include regions of overlap 33. By this it is meant that at least two of the segments may be configured to operatively engage the same body of at least one bracket during use of the device to adjust a plurality of brackets within the patient's mouth. For example, after utilizing a first segment to adjust the relative orientation of at least one body/bracket, and optionally a plurality of bodies/brackets, the brackets may be configured to a locked configuration and the segment may be disengaged. A different segment of the orthodontic prescription-defining device 30 may then be engaged to at least one of the adjusted brackets, which optionally may serve as a reference point, and at least one to-be-adjusted bracket.

In FIG. 10, orthodontic prescription-defining device 30 of orthodontic appliance system 20 is disengaged from orthodontic brackets 50. In FIG. 11, orthodontic prescription-defining device 30 is operatively contacting at least one intra-oral reference point (as illustrated in FIGS. 2-4 and 8 and discussed herein) and also is operatively engaged with at least one orthodontic bracket 50 and/or with archwire 40. As discussed, the orthodontic bracket may be transitioned to an unlocked configuration prior to and/or during operative engagement of orthodontic prescription-defining device 30 with the teeth, with the orthodontic brackets, and/or with the archwire. This may permit the orthodontic prescription-defining device to translate, move, and/or relocate an archwire slot of the orthodontic bracket to a predetermined relative orientation with respect to a base of the orthodontic bracket. Subsequently, the orthodontic bracket may be transitioned to a locked configuration. This may retain the archwire slot of the orthodontic bracket in the predetermined relative orientation despite disengagement of orthodontic prescription-defining device 30 from the teeth, from the orthodontic bracket, and/or from the archwire.

Figure 12:
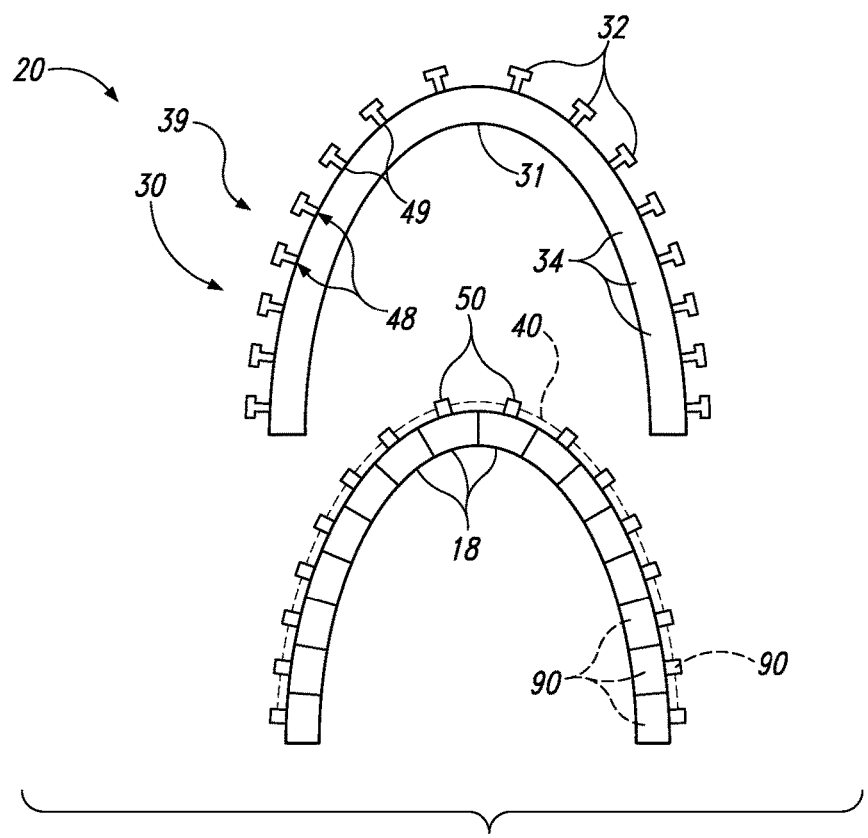
FIG. 12 is a schematic representation of examples of an orthodontic appliance system according to the present disclosure, as viewed from the gingival direction and with an orthodontic prescription-defining device disengaged from a plurality of orthodontic brackets.

FIG. 12 is a schematic representation of examples of an orthodontic appliance system 20, according to the present disclosure, as viewed from the gingival direction. System 20 of FIG. 12 includes another orthodontic prescription-defining device 30 that is disengaged from a plurality of orthodontic brackets 50. As illustrated in FIG. 12, device 30 may include and/or be a composite prescription-defining device 30 that includes a contacting body 31 and a plurality of engagement structures 32. Engagement structures 32 may be operatively attached to contacting body 31, such as via an attachment structure 48, such as a pivot structure 49. Contacting body 31 may define a plurality of contacting structures 34 that may be shaped to interface with corresponding intra-oral reference points 90.

Figures 13, 14:
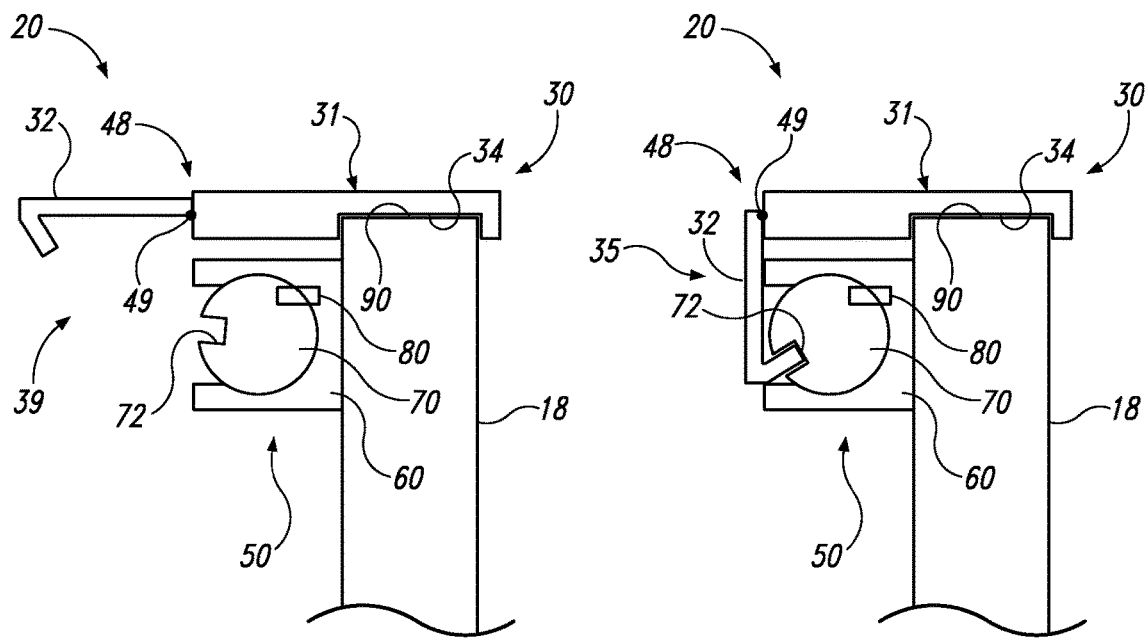
FIG. 13 is a schematic cross-sectional view of the orthodontic appliance system of FIG. 12 illustrating a prescription-defining engagement structure disengaged from an orthodontic bracket.
FIG. 14 is a schematic cross-sectional view of the orthodontic appliance system of FIG. 12 illustrating a prescription-defining engagement structure engaged with an orthodontic bracket and urging an archwire slot of the orthodontic bracket to a preselected orientation.

FIGS. 13-14 are schematic cross-sectional views of an embodiment of the orthodontic appliance system of FIG. 12 in which a prescription-defining engagement structure 32 directly and operatively engages a corresponding orthodontic bracket 50 to urge a corresponding archwire slot 72 to a respective preselected orientation. FIG. 13 illustrates the prescription-defining engagement structure disengaged from the corresponding orthodontic bracket (i.e., in a disengaged configuration 39), while FIG. 14 illustrates the prescription-defining engagement structure engaged with the corresponding orthodontic bracket (i.e., in an engaged configuration 35). As illustrated by FIGS. 13-14, engagement of engagement structure 32 with archwire slot 72 of orthodontic bracket 50 may change an orientation of archwire slot 72, may urge archwire slot 72 from a first orientation to a second orientation, and/or may urge archwire slot to a preselected orientation that may be defined by a shape and/or geometry of device 30.

Figure 15:
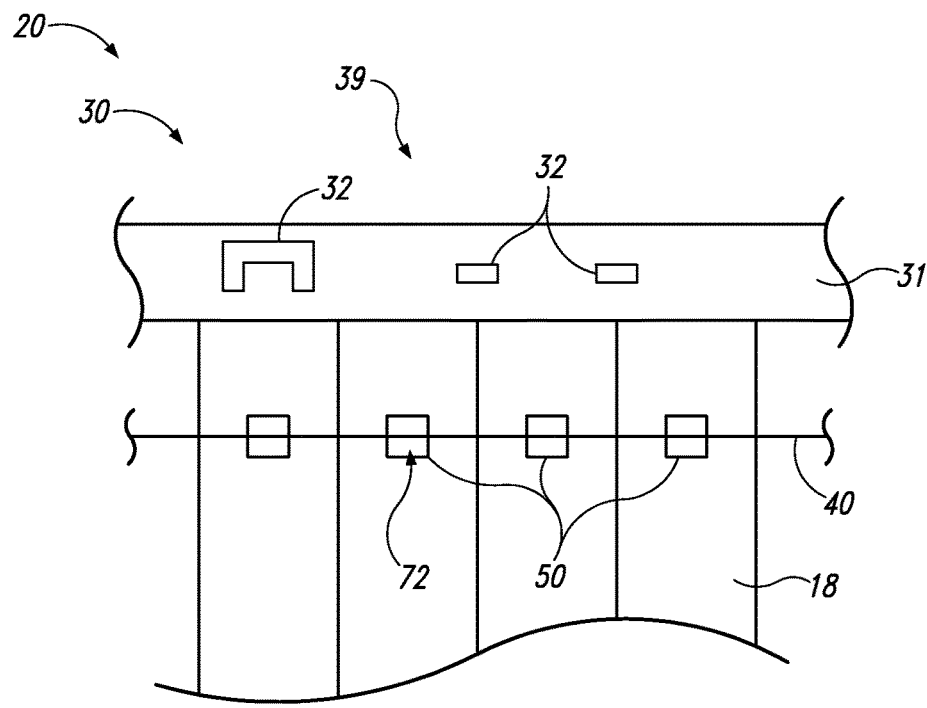
FIG. 15 is a schematic illustration of the orthodontic appliance system of FIG. 12, as viewed from the labial, lingual, and/or buccal directions, and illustrating a prescription-defining engagement structure disengaged from an archwire.
Figure 16:
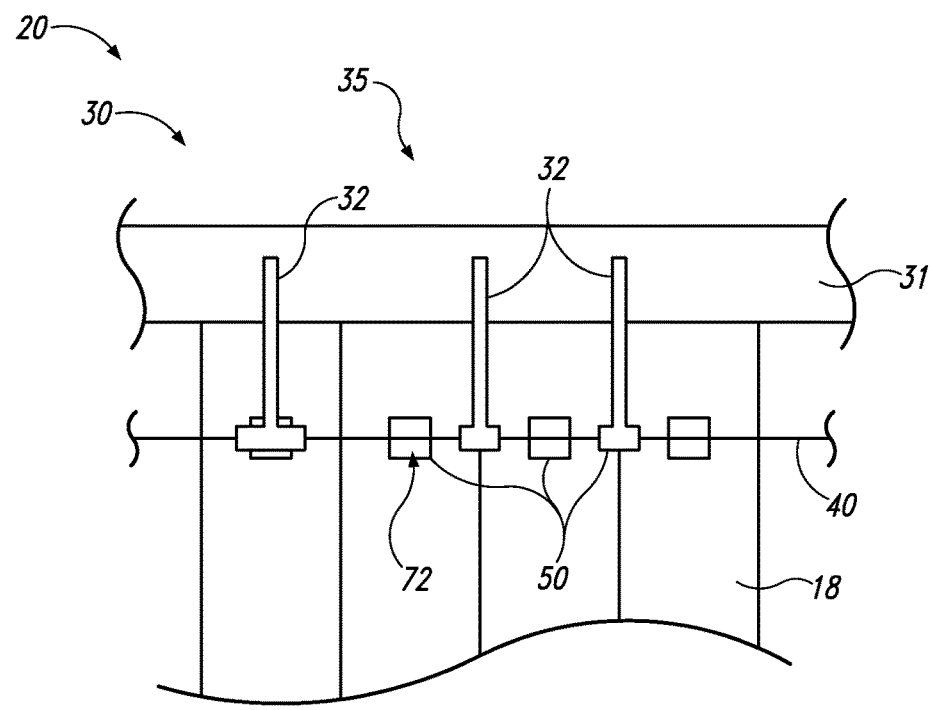
FIG. 16 is a schematic illustration of the orthodontic appliance system of FIG. 12, as viewed from the labial, lingual, and/or buccal directions, and illustrating a prescription-defining engagement structure engaged with an archwire and urging an archwire slot of at least one orthodontic bracket to a preselected orientation.

FIGS. 15-16 are schematic illustrations of an embodiment of the orthodontic appliance system of FIG. 12, as viewed from the labial, lingual, and/or buccal directions, in which a plurality of prescription-defining engagement structures 32 directly and operatively engages an archwire 40 to urge one or more archwire slots 72 to respective preselected orientations. FIG. 15 illustrates prescription-defining engagement structures 32 disengaged from archwire 40 (i.e., in a disengaged configuration 39), while FIG. 16 illustrates the prescription-defining engagement structures engaged with the corresponding orthodontic brackets (i.e., in an engaged configuration 35). When prescription-defining engagement structures 32 are engaged with archwire 40, the prescription-defining engagement structures may bend, bow, twist, and/or otherwise distort archwire 40, which may, in turn, change an orientation of archwire slots 72 of orthodontic brackets 50.

Figure 17:
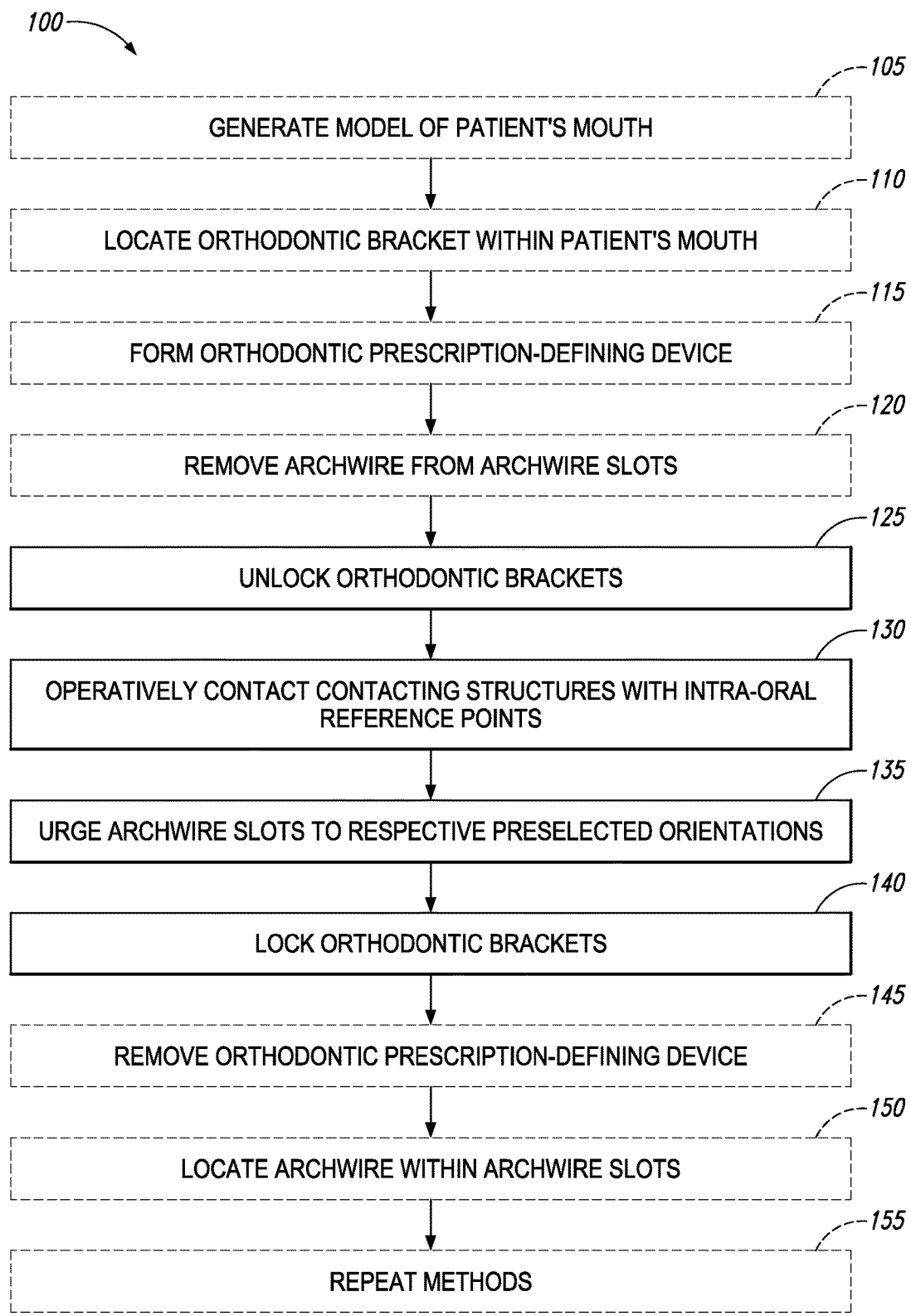
FIG. 17 is a flowchart depicting methods according to the present disclosure, of adjusting an orientation of a plurality of archwire slots of a plurality of orthodontic brackets.

FIG. 17 is a flowchart depicting methods 100, according to the present disclosure, of adjusting an orientation of a plurality of archwire slots of a plurality of orthodontic brackets. The adjusting may include adjusting to define a prescription of the plurality of orthodontic brackets and may be performed while each of the plurality of orthodontic brackets is operatively affixed to a corresponding tooth within a patient's mouth. Each orthodontic bracket includes a base that is configured to be operatively affixed to the corresponding tooth and a body that is configured to be selectively repositioned relative to the base. The body defines an archwire slot that is configured to receive an archwire. Each orthodontic bracket defines a locked configuration, in which an orientation of the archwire slot relative to the base is at least substantially fixed. Each orthodontic bracket also defines an unlocked configuration, which permits the orientation of the archwire slot relative to the base to be varied via relative motion between the body and the base.

Methods 100 may include generating a model of the patient's mouth at 105 and/or locating an orthodontic bracket within the patient's mouth at 110. Methods 100 further may include forming an orthodontic prescription-defining device at 115 and/or removing the archwire from the archwire slots at 120. Methods 100 include unlocking the orthodontic brackets at 125, operatively contacting a plurality of contacting structures with a plurality of intra-oral reference points at 130, urging the archwire slots to respective preselected orientations at 135, and locking the orthodontic brackets at 140. Methods 100 further may include removing the orthodontic prescription-defining device at 145, locating the archwire within the archwire slots at 150, and/or repeating the methods at 155.

Generating the model of the patient's mouth at 105 may include generating any suitable model and/or representation of the patient's mouth in any suitable manner. As examples, the generating at 105 may include generating a three-dimensional model of the patient's mouth, generating a digital model of the patient's mouth, digitally scanning the patient's mouth, generating a mold of the patient's mouth, and/or generating a casting of the patient's mouth.

Locating the orthodontic bracket within the patient's mouth at 110 may include locating and/or placing the orthodontic bracket, or a plurality of orthodontic brackets, within the patient's mouth. This may include operatively affixing and/or cementing the orthodontic bracket to the tooth and/or to a band or other intermediate structure that is secured to and/or around the tooth. It is within the scope of the present disclosure that the locating at 110 may be based, at least in part, on the generating at 105. As an example, a location and/or orientation of the orthodontic bracket on the tooth may be selected based, at least in part, on the generating at 105.

It is further within the scope of the present disclosure that the locating at 110 may include locating the orthodontic bracket in any suitable manner. As an example, the locating at 110 may include manually locating the orthodontic bracket on the patient's tooth. As another example, the locating at 110 may include manually and/or sequentially locating the plurality of orthodontic brackets on respective teeth. As yet another example, the locating at 110 may include simultaneously locating the plurality of orthodontic brackets on the respective teeth, such as through the use of a pick-up impression and/or a jig. This may include simultaneously locating every orthodontic bracket that may be utilized in the patient's mouth and/or that may be included in an overall orthodontic appliance system. Additionally or alternatively, this also may include simultaneously locating a subset of the orthodontic brackets. Methods 100 according to the present disclosure additionally or alternatively may commence with the patient's teeth already modelled and/or with the bracket(s) already positioned on the patient's tooth/teeth.

Forming the orthodontic prescription-defining device at 115 may include forming the orthodontic prescription-defining device in any suitable manner and/or based upon any suitable criteria. As an example, the forming at 115 may include forming such that the orthodontic prescription-defining device establishes the preselected relative orientations between the archwire slots and the bases of the corresponding orthodontic brackets during and/or responsive to the operatively contacting at 130 and the urging at 135.

As another example, the forming at 115 may include forming based, at least in part, on the generating at 105 and/or on the model that is generated during the generating at 105. As additional examples, the forming at 115 may include forming based, at least in part, on (or forming such that the preselected relative orientation is based, at least in part on) a three-dimensional model of the tooth, on a three-dimensional model of a location of the tooth relative to at least one other tooth of the patient, on an initial occlusion of the tooth, on a desired occlusion of the tooth, on a location of the orthodontic bracket on the tooth, and/or on a relative orientation between the orthodontic bracket and/or the archwire slot thereof and the intra-oral reference point. As discussed in more detail herein, the orthodontic prescription-defining device may define the preselected relative orientation prior to at least the operatively contacting at 130, the urging at 135, and/or the locking at 140.

Removing the archwire from the archwire slots at 120 may include removing prior to the operatively contacting at 130, removing to facilitate the operatively contacting at 130, removing prior to the urging at 135, and/or removing to facilitate the urging at 135. As an example, and during the urging at 135, the prescription-defining device may be configured to directly and operatively engage the archwire slots of the orthodontic brackets. Under these conditions, the removing at 120 may provide clearance for the prescription-defining device to directly and operatively engage the archwire slots. However, this is not required. Thus, methods 100 additionally or alternatively may include performing the operatively contacting at 130 and the urging at 135 while the archwire extends within the archwire slots. This may include directly and operatively engaging the archwire slot with the prescription-defining device while the archwire extends within the archwire slot and/or directly and operatively engaging a portion of the archwire that is external to the archwire slot with the prescription-defining device.

Unlocking the orthodontic brackets at 125 may include unlocking each of the plurality of orthodontic brackets, such as by transitioning each of the plurality of orthodontic brackets to a respective unlocked configuration and/or ensuring that each of the plurality of orthodontic brackets is in the corresponding unlocked configuration. This may include transitioning such that the orthodontic brackets permit the orientation of the corresponding archwire slots relative to the corresponding bases to be varied.

The unlocking at 125 may be performed prior to the operatively contacting at 130, prior to the urging at 135, concurrently with the operatively contacting at 130, and/or concurrently with the urging at 135 and may be accomplished in any suitable manner. As an example, the unlocking at 125 may include transitioning, translating, and/or moving a retention structure to permit the archwire slot to move relative to the base. As a more specific example, the unlocking at 125 may include manually transitioning the orthodontic bracket prior to the operatively contacting at 130 and/or prior to the urging at 135. As another more specific example, the orthodontic bracket may be configured to transition to the unlocked configuration responsive to and/or as a result of the operatively contacting at 130 and/or the urging at 135.

Operatively contacting the plurality of contacting structures with the plurality of intra-oral reference points at 130 may include operatively contacting to define a predetermined, specified, and/or selected orientation, or relative orientation, of the orthodontic prescription-defining device within the patient's mouth. Additionally or alternatively, the operatively contacting at 130 may include operatively contacting to align the orthodontic prescription-defining device, operatively contacting to establish a reference point for the orthodontic prescription-defining device, and/or operatively contacting to establish a reference orientation for the orthodontic prescription-defining device. The intra-oral reference point may include and/or be any suitable intra-oral reference point, examples of which are disclosed herein.

Urging the archwire slots to respective preselected orientations at 135 may include urging each of the plurality of archwire slots with a corresponding plurality of prescription-defining engagement structures of the orthodontic prescription-defining device. The respective preselected orientations may be defined and/or referenced relative to the bases of the brackets, relative to the plurality of intra-oral reference points, and/or relative to any suitable reference orientation. The urging at 135 may include operatively engaging the orthodontic prescription-defining device with any suitable portion of the orthodontic bracket and/or with the archwire and may be performed at least partially concurrently with and/or responsive to the operatively contacting at 130. This may include operatively engaging the orthodontic prescription-defining device with the orthodontic bracket and/or with the archwire while the orthodontic bracket is in the unlocked configuration and/or while the orthodontic bracket permits the relative orientation of the archwire slot and the base to be varied. Examples of portions of the orthodontic bracket and/or of the archwire that may be operatively engaged by the orthodontic prescription-defining device are discussed herein.

The urging at 135 may include changing and/or adjusting the orientation of at least a portion of the plurality of archwire slots to change and/or adjust any suitable tip, torque, and/or rotational prescriptive force that may be imparted on and/or applied to the tooth by an archwire that may subsequently be located in the archwire slots (such as during the locating at 150) and/or that presently extends within the archwire slots. The urging at 135 further may include urging such that each of the archwire slots and the corresponding bases defines the respective preselected orientation therebetween. The respective preselected orientations may be defined relative to the intra-oral reference point and/or may be defined and/or established by the orthodontic prescription-defining device.

It is within the scope of the present disclosure that the urging at 135 may include changing an orientation of at least one archwire slot relative to at least one other archwire slot. The urging at 135 may include simultaneously urging each of the plurality of archwire slots. Alternatively, the urging at 135 also may include sequentially, consecutively, and/or successively urging each of the plurality of archwire slots while the orthodontic prescription-defining device is operatively contacting the plurality of intra-oral reference points. This may include urging subsequent to initiating contact between the plurality of contacting structures and the plurality of intra-oral reference points and/or prior to the removing at 145.

As discussed, the urging at 135 may include directly and operatively engaging at least one of the plurality of engagement structures with a corresponding orthodontic bracket. This may include directly and operatively engaging any suitable reference structure, such as the archwire slot, of the corresponding orthodontic bracket.

Additionally or alternatively, and as also discussed, the urging at 135 may include directly and operatively engaging at least one of the plurality of engagement structures with the archwire. Under these conditions, the orthodontic prescription-defining device may indirectly urge the plurality of archwire slots to the respective preselected orientations. The archwire may be engaged by the engagement structure in any suitable manner. As an example, the engagement structure may clamp, or clamp around, the archwire. When the urging at 135 includes engaging the archwire, the engagement structure may be configured to twist, bend, and/or deform the archwire to thereby (indirectly) change the orientation of one or more of the archwire slots.

Locking the orthodontic brackets at 140 may include locking each of the plurality of orthodontic brackets, such as by transitioning each of the plurality of orthodontic brackets to a respective locked configuration and/or ensuring that each of the plurality of orthodontic brackets is in the corresponding locked configuration. This may include transitioning such that each of the orthodontic brackets retains the corresponding archwire slot in a fixed, or at least substantially fixed, orientation relative to the corresponding base and/or relative to the plurality of intra-oral reference points.

The locking at 140 may be performed subsequent to the urging at 135 and/or during the operatively contacting at 130 and may be accomplished in any suitable manner. As an example, the locking at 140 may include transitioning, translating, and/or moving the retention structure to restrict motion of the archwire slot relative to the base. As a more specific example, the locking at 140 may include manually transitioning the orthodontic bracket subsequent to the urging at 135. As another more specific example, the orthodontic bracket may be configured to transition to the locked configuration responsive to and/or as a result of the removing at 145, and the locking at 140 may include locking at least partially concurrently with the removing at 145.

Removing the orthodontic prescription-defining device at 145 may include disengaging the orthodontic prescription-defining device from the plurality of orthodontic brackets, from the archwire, and/or from the plurality of intra-oral reference points and may be accomplished in any suitable manner. As an example, the removing at 145 may include separating the orthodontic prescription-defining device from the plurality of intra-oral reference points. As another example, the removing at 145 also may include separating the orthodontic prescription-defining device from the plurality of orthodontic brackets. As yet another example, the removing at 145 may include removing the orthodontic prescription-defining device from the patient's mouth.

Locating the archwire within the archwire slots at 150 may include locating and/or otherwise placing any suitable archwire within the plurality of archwire slots such that the archwire applies one or more prescriptive forces to the teeth via the orthodontic brackets. This may include locating a round, square, and/or rectangular archwire within round, square, and/or rectangular archwire slots such that the archwire applies tip, torque, and/or rotational forces to the teeth. As discussed, it also is within the scope of the present disclosure that removal of an archwire from the archwire slot is not required prior to the operatively contacting at 130, the urging at 135, the locking at 140, and/or the removing at 145. In such a method, it follows that the locating at 150 is not required, although in some methods, an archwire may be removed and replaced, such as to inspect/adjust the archwire (such as any bends in the archwire) and/or to replace the archwire with a different archwire, such as with an archwire with a different thickness, stiffness, shape, bends, etc.

Repeating the methods at 155 may include repeating any suitable portion of methods 100 in any suitable sequence. As an example, the orthodontic prescription-defining device may be a first orthodontic prescription-defining device that defines a first preselected relative orientation between the archwire slot and the base. Under these conditions, the repeating at 155 may include repeating at least the unlocking at 125, the operatively contacting at 130, the urging at 135, and/or the locking at 140 with a second orthodontic prescription-defining device that is different from the first orthodontic prescription-defining device and/or that defines a second preselected relative orientation between the archwire slot and the base. The second preselected relative orientation may be different from the first preselected relative orientation. As discussed herein, this process may be repeated any suitable number of times over the course of an orthodontic treatment plan to progressively, sequentially, and/or systematically vary the prescriptive forces that are applied to the tooth and/or to move the tooth from a current, present, and/or initial occlusion to a target and/or desired occlusion.

When the method is repeated, the archwire may be removed from the archwire slot, for example, prior to or after the unlocking at 125. Alternatively, the archwire may remain in the archwire slot, as discussed.

As a more specific example, an orthodontist may perform the locating at 110 during a first office visit. The orthodontist also may perform at least the unlocking at 125, the operatively contacting at 130, the urging at 135, and the locking at 140 to establish a first preselected relative orientation between the archwire slot and the base. The orthodontist then may perform the locating at 150 to locate a first archwire, such as a circular cross-section 0.014" diameter nickel titanium archwire, in the archwire slot to apply a first set of prescriptive forces to the tooth. The first archwire may be left in the archwire slot for a first treatment time, such as 10 weeks.

Subsequently, during a second office visit, the orthodontist may perform the removing at 120 to remove the first archwire from the archwire slot. The orthodontist also may repeat at least the unlocking at 125, the operatively contacting at 130, the urging at 135, and the locking at 140 to establish a second preselected relative orientation between the archwire slot and the base. The orthodontist then may perform the locating at 150 to locate a second archwire, such as a rectangular cross-section 0.014"×0.025" nickel titanium archwire, in the archwire slot to apply a second set of prescriptive forces to the tooth. The second archwire may be left in the archwire slot for a second treatment time, such as 8-10 weeks.

During a third office visit, the orthodontist may perform the removing at 120 to remove the second archwire from the archwire slot. The orthodontist also may repeat at least the unlocking at 125, the operatively contacting at 130, the urging at 135, and the locking at 140 to establish a third preselected relative orientation between the archwire slot and the base. The orthodontist then may perform the locating at 150 to locate a third archwire, such as a rectangular cross-section 0.018"×0.025" nickel titanium archwire, in the archwire slot to apply a third set of prescriptive forces to the tooth. The third archwire may be left in the archwire slot for a third treatment time, such as 6-8 weeks.

This process may be repeated any suitable number of times until the tooth reaches a desired and/or target occlusion. During any given office visit, the original archwire may be re-used or a new archwire may be installed. During any given office visit, the orthodontic bracket may be removed from the tooth and the same orthodontic bracket, or a different orthodontic bracket, may be operatively affixed to (a different location on) the tooth, such as by repeating the locating at 110. During any given office visit, the generating at 105 may be repeated and/or the model may be utilized during the locating at 110 and/or during the forming at 115.

As another more specific example, the orthodontic prescription-defining device may be a first orthodontic prescription-defining device that is configured to urge a first plurality of orthodontic brackets to the corresponding preselected orientations. Under these conditions, the repeating at 155 may include repeating the unlocking at 125, the operatively contacting at 130, the urging at 135, and/or the locking at 140 with a second orthodontic prescription-defining device to urge a second plurality of orthodontic brackets to corresponding preselected orientations. The first plurality of orthodontic brackets may be different from the second plurality of orthodontic brackets and/or may be spaced-apart from the second plurality of orthodontic brackets within the patient's mouth.

In the preceding discussion, references to sequential steps and/or orientations (e.g., first, second, third, etc.) are intended to indicate a relative successive order (first, then second, then third, etc.). The indicated steps and/or orientations may occur consecutively, but it also is within the scope of the present disclosure that one or more intermediate steps and/or orientations may be utilized so long as the described sequences of steps and/or orientations is maintained.

In the present disclosure, several of the illustrative, non-exclusive examples have been discussed and/or presented in the context of flow diagrams, or flow charts, in which the methods are shown and described as a series of blocks, or steps. Unless specifically set forth in the accompanying description, it is within the scope of the present disclosure that the order of the blocks may vary from the illustrated order in the flow diagram, including with two or more of the blocks (or steps) occurring in a different order and/or concurrently.

As used herein, the term "and/or" placed between a first entity and a second entity means one of (1) the first entity, (2) the second entity, and (3) the first entity and the second entity. Multiple entities listed with "and/or" should be construed in the same manner, i.e., "one or more" of the entities so conjoined. Other entities may optionally be present other than the entities specifically identified by the "and/or" clause, whether related or unrelated to those entities specifically identified. Thus, as a non-limiting example, a reference to "A and/or B," when used in conjunction with open-ended language such as "comprising" may refer, in one embodiment, to A only (optionally including entities other than B); in another embodiment, to B only (optionally including entities other than A); in yet another embodiment, to both A and B (optionally including other entities). These entities may refer to elements, actions, structures, steps, operations, values, and the like.

As used herein, the phrase "at least one," in reference to a list of one or more entities should be understood to mean at least one entity selected from any one or more of the entity in the list of entities, but not necessarily including at least one of each and every entity specifically listed within the list of entities and not excluding any combinations of entities in the list of entities. This definition also allows that entities may optionally be present other than the entities specifically identified within the list of entities to which the phrase "at least one" refers, whether related or unrelated to those entities specifically identified. Thus, as a non-limiting example, "at least one of A and B" (or, equivalently, "at least one of A or B," or, equivalently "at least one of A and/or B") may refer, in one embodiment, to at least one, optionally including more than one, A, with no B present (and optionally including entities other than B); in another embodiment, to at least one, optionally including more than one, B, with no A present (and optionally including entities other than A); in yet another embodiment, to at least one, optionally including more than one, A, and at least one, optionally including more than one, B (and optionally including other entities). In other words, the phrases "at least one," "one or more," and "and/or" are open-ended expressions that are both conjunctive and disjunctive in operation. For example, each of the expressions "at least one of A, B and C," "at least one of A, B, or C," "one or more of A, B, and C," "one or more of A, B, or C" and "A, B, and/or C" may mean A alone, B alone, C alone, A and B together, A and C together, B and C together, A, B and C together, and optionally any of the above in combination with at least one other entity.

In the event that any patents, patent applications, or other references are incorporated by reference herein and (1) define a term in a manner that is inconsistent with and/or (2) are otherwise inconsistent with, either the non-incorporated portion of the present disclosure or any of the other incorporated references, the non-incorporated portion of the present disclosure shall control, and the term or incorporated disclosure therein shall only control with respect to the reference in which the term is defined and/or the incorporated disclosure was present originally.

As used herein the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function but that the element, component, and/or other subject matter is specifically selected, created, implemented, utilized, programmed, and/or designed for the purpose of performing the function. It is also within the scope of the present disclosure that elements, components, and/or other recited subject matter that is recited as being adapted to perform a particular function may additionally or alternatively be described as being configured to perform that function, and vice versa.

As used herein, the phrase, "for example," the phrase, "as an example," and/or simply the term "example," when used with reference to one or more components, features, details, structures, embodiments, and/or methods according to the present disclosure, are intended to convey that the described component, feature, detail, structure, embodiment, and/or method is an illustrative, non-exclusive example of components, features, details, structures, embodiments, and/or methods according to the present disclosure. Thus, the described component, feature, detail, structure, embodiment, and/or method is not intended to be limiting, required, or exclusive/exhaustive; and other components, features, details, structures, embodiments, and/or methods, including structurally and/or functionally similar and/or equivalent components, features, details, structures, embodiments, and/or methods, are also within the scope of the present disclosure.

Examples of systems, devices, and methods according to the present disclosure are presented in the following enumerated paragraphs. It is within the scope of the present disclosure that an individual step of a method recited herein, including in the following enumerated paragraphs, may additionally or alternatively be referred to as a "step for" performing the recited action.

A1. An orthodontic prescription-defining device configured to concurrently adjust an orientation of a plurality of archwire slots of a plurality of orthodontic brackets while each of the plurality of orthodontic brackets is operatively affixed to a corresponding tooth within a patient's mouth, the device comprising:

a plurality of contacting structures, wherein each of the plurality of contacting structures is configured to operatively contact a respective predetermined intra-oral reference point of a plurality of intra-oral reference points within the patient's mouth to define a predetermined orientation of the orthodontic prescription-defining device within the patient's mouth; and a plurality of prescription-defining engagement structures;

wherein each of the plurality of orthodontic brackets includes a base configured to be operatively affixed to the corresponding tooth and a body that is configured to be selectively repositioned relative to the base and defines an archwire slot of the plurality of archwire slots that is configured to receive an archwire;

wherein each of the plurality of orthodontic brackets defines a locked configuration in which an orientation of the archwire slot relative to the base is at least substantially fixed;

wherein each of the plurality of orthodontic brackets further defines an unlocked configuration that permits the orientation of the archwire slot relative to the base to be varied via relative motion between the body and the base; and wherein, when each of the plurality of orthodontic brackets is in a respective unlocked configuration, each of the plurality of engagement structures is configured to urge at least one archwire slot of the plurality of archwire slots to a respective preselected orientation between the at least one archwire slot and the plurality of intra-oral reference points.

A2. The device of paragraph A1, wherein each of the plurality of engagement structures is configured to operatively contact a respective body of a respective orthodontic bracket of the plurality of orthodontic brackets to urge a respective archwire slot of the plurality of archwire slots to the respective preselected orientation.

A3. The device of any of paragraphs A1-A2, wherein each of the plurality of engagement structures is configured to be received within a/the respective archwire slot of a/the respective orthodontic bracket of the plurality of orthodontic brackets to urge the respective archwire slot to the respective preselected orientation.

A4. The device of any of paragraphs A1-A3, wherein each of the plurality of engagement structures is configured to operatively contact a portion of the archwire proximate a/the respective archwire slot of a/the respective orthodontic bracket to urge the respective archwire slot of the plurality of archwire slots to the respective preselected orientation.

A5. The device of any of paragraphs A1-A4, wherein each of the plurality of engagement structures is configured to urge the at least one archwire slot to the respective preselected orientation while the archwire is received within the archwire slot.

A6. The device of any of paragraphs A1-A5, wherein each of the plurality of engagement structures is configured to urge the at least one archwire slot to the respective preselected orientation subsequent to the archwire being removed from the archwire slot.

A7. The device of any of paragraphs A1-A6, wherein the orthodontic prescription-defining device is shaped to define the respective preselected orientation prior to contact between each of the plurality of contacting structures and the respective predetermined intra-oral reference point.

A8. The device of any of paragraphs A1-A7, wherein the orthodontic prescription-defining device is shaped to define the respective preselected orientation prior to urging the at least one archwire slot to the respective preselected orientation.

A9. The device of any of paragraphs A1-A8, wherein each of the plurality of orthodontic brackets is configured to provide at least 1, at least 2, at least 3, at least 4, at least 5, or 6 degrees of freedom between a respective archwire slot and a respective base, and further wherein each of the plurality of engagement structures is configured to urge the at least one archwire slot via motion of a respective body that defines the at least one archwire slot in at least 1, at least 2, at least 3, at least 4, at least 5, or 6 degrees of freedom.

A10. The device of any of paragraphs A1-A9, wherein each of the plurality of engagement structures is configured to define a single preselected orientation between the at least one archwire slot and a corresponding base of a corresponding orthodontic bracket.

A11. The device of any of paragraphs A1-A10, wherein the orthodontic prescription-defining device is a monolithic orthodontic prescription-defining device that defines the plurality of contacting structures and the plurality of engagement structures.

A12. The device of any of paragraphs A1-A11, wherein the orthodontic prescription-defining device is a composite structure that includes a contacting body that defines the plurality of contacting structures and is operatively attached to the plurality of engagement structures.

A13. The device of paragraph A12, wherein each of the plurality of engagement structures is configured to be selectively transitioned between a disengaged configuration and an engaged configuration, wherein, when a respective engagement structure of the plurality of engagement structures is in the engaged configuration, the respective engagement structure is configured to urge the at least one archwire slot to the respective preselected orientation.

A14. The device of any of paragraphs A1-A13, wherein the plurality of intra-oral reference points includes at least one of:

(i) a portion of at least one tooth within the patient's mouth;
(ii) an occlusal surface of the at least one tooth;
(iii) a cusp tip of the at least one tooth;
(iv) a buccal-lingual surface of the at least one tooth;
(v) a portion of at least one orthodontic bracket of the plurality of orthodontic brackets; and
(vi) a base of the at least one orthodontic bracket.

A15. The device of any of paragraphs A1-A14, wherein a conformation of the orthodontic prescription-defining device is selected based, at least in part, on at least one of:

(i) a three-dimensional model of the patient's mouth;
(ii) a three-dimensional model of the respective predetermined intra-oral reference point associated with each of the plurality of contacting structures;
(iii) a three-dimensional model of the plurality of orthodontic brackets while each of the plurality of orthodontic brackets is operative affixed to a corresponding tooth;
(iv) a three-dimensional model of the plurality of archwire slots;
(v) an initial occlusion of at least one tooth;
(vi) a current occlusion of at least one tooth;
(vii) a desired occlusion of at least one tooth; and
(viii) a location of each of the plurality of orthodontic brackets on the corresponding tooth.

A16. The device of any of paragraphs A1-A15, wherein the plurality of contacting structures includes at least 2, at least 3, at least 4, at least 5, at least 6, at least 8, at least 10, at least 12, or at least 14 contacting structures.

A17. The device of any of paragraphs A1-A16, wherein the plurality of engagement structures includes at least 2, at least 3, at least 4, at least 5, at least 6, at least 8, at least 10, at least 12, or at least 14 engagement structures.

A18. The device of any of paragraphs A1-A17, wherein each of the plurality of engagement structures is configured to urge the at least one archwire slot to the respective preselected orientation concurrently with a remainder of the plurality of engagement structures.

B1. An orthodontic appliance system, comprising:

the orthodontic prescription-defining device of any of paragraphs A1-A18; and the plurality of orthodontic brackets of any of paragraphs A1-A18.

B2. The system of paragraph B1, wherein the orthodontic prescription-defining device is a first orthodontic prescription-defining device, wherein the system includes a plurality of orthodontic prescription-defining devices, and further wherein each of the plurality of orthodontic prescription-defining devices defines a respective preselected orientation of each of the plurality of archwire slots.

B3. The system of paragraph B2, wherein the respective preselected orientation defined by each of the plurality of orthodontic prescription-defining devices is different from a respective preselected orientation defined by a remainder of the plurality of orthodontic prescription-defining devices.

B4. The system of any of paragraphs B2-B3, wherein the plurality of orthodontic prescription-defining devices defines a progressive prescription sequence that is configured to apply a sequence of prescriptive forces to a plurality of teeth to progressively move the plurality of teeth from an initial occlusion to a desired occlusion.

B5. The system of any of paragraphs B1-B4, wherein the system further includes an orthodontic prescription-defining device fabrication assembly that is configured to be utilized by an orthodontist to create the orthodontic prescription-defining device, and optionally wherein the orthodontic prescription-defining device fabrication assembly includes a three-dimensional printer.

B6. The system of any of paragraphs B1-B5, wherein the system includes a plurality of orthodontic prescription-defining devices, wherein each of the plurality of orthodontic prescription-defining devices is configured to urge a respective subset of the plurality of archwire slots to a corresponding respective preselected orientation.

C1. A method of adjusting an orientation of a plurality of archwire slots of a plurality of orthodontic brackets to define a prescription of the plurality of orthodontic brackets while each of the plurality of orthodontic brackets is operatively affixed to a corresponding tooth within a patient's mouth, wherein each of the plurality of orthodontic brackets includes a base configured to be operatively affixed to the corresponding tooth and a body that is configured to be selectively repositioned relative to the base and that defines an archwire slot of the plurality of archwire slots that is configured to receive an archwire, and further wherein each of the plurality of orthodontic brackets defines a locked configuration in which an orientation of the archwire slot relative to the base is at least substantially fixed, and an unlocked configuration that permits the orientation of the archwire slot relative to the base to be varied via relative motion between the body and the base, the method comprising:

unlocking each of the plurality of orthodontic brackets by transitioning each of the plurality of orthodontic brackets to a respective unlocked configuration;

operatively contacting a plurality of contacting structures of an orthodontic prescription-defining device with a plurality of intra-oral reference points within the patient's mouth to define a predetermined orientation of the orthodontic prescription-defining device within the patient's mouth;

concurrently with the operatively contacting, urging, with a plurality of prescription-defining engagement structures of the orthodontic prescription-defining device, each of the plurality of archwire slots to a respective preselected orientation relative to the plurality of intra-oral reference points; and locking each of the plurality of orthodontic brackets by transitioning each of the plurality of orthodontic brackets to a respective locked configuration.

C2. The method of paragraph C1, wherein the operatively contacting includes operatively contacting at least one of:

(i) a portion of at least one tooth within the patient's mouth;

(ii) an occlusal surface of the at least one tooth;

(iii) a cusp tip of the at least one tooth;

(iv) a buccal-lingual surface of the at least one tooth;

(v) a portion of at least one orthodontic bracket of the plurality of orthodontic brackets; and (vi) a base of the at least one orthodontic bracket.

C3. The method of any of paragraphs C1-C2, wherein the urging includes changing an orientation of at least one of the plurality of archwire slots relative to at least one other of the plurality of archwire slots.

C4. The method of any of paragraphs C1-C3, wherein the urging includes simultaneously urging each of the plurality of archwire slots to the respective preselected orientation.

C5. The method of any of paragraphs C1-C4, wherein the urging is responsive to the operatively contacting.

C6. The method of any of paragraphs C1-C5, wherein the urging is subsequent to initiating contact between the plurality of contacting structures and the plurality of intra-oral reference points.

C7. The method of any of paragraphs C1-C6, wherein the urging includes directly and operatively engaging at least one of the plurality of engagement structures with a corresponding orthodontic bracket of the plurality of orthodontic brackets.

C8. The method of paragraph C7, wherein the directly and operatively engaging includes directly and operatively engaging at least one of:

(i) a reference structure of the corresponding orthodontic bracket; and (ii) an archwire slot of the corresponding orthodontic bracket.

C9. The method of any of paragraphs C1-C8, wherein the urging includes directly and operatively engaging the archwire to indirectly urge each of the plurality of archwire slots to the respective preselected orientation.

C10. The method of paragraph C9, wherein the directly and operatively engaging the archwire includes clamping at least one of the plurality of engagement structures to the archwire.

C11. The method of any of paragraphs C9-C10, wherein the directly and operatively engaging the archwire includes at least one of twisting the archwire, bending the archwire, and deforming the archwire.

C12. The method of any of paragraphs C1-C11, wherein, prior to the operatively contacting, the method further includes removing the archwire from the plurality of archwire slots.

C13. The method of any of paragraphs C1-C12, wherein, subsequent to the locking, the method further includes locating the archwire within the plurality of archwire slots.

C14. The method of any of paragraphs C1-C13, wherein the method includes performing at least the operatively contacting and the urging while the archwire extends within the plurality of archwire slots.

C15. The method of any of paragraphs C1-C14, wherein a preselected orientation of a first orthodontic bracket of the plurality of orthodontic brackets is different from a preselected orientation of a second orthodontic bracket of the plurality of orthodontic brackets.

C16. The method of any of paragraphs C1-C15, wherein, subsequent to the locking, the method further includes separating the orthodontic prescription-defining device from the plurality of intra-oral reference points and from the plurality of orthodontic brackets.

C17. The method of any of paragraphs C1-C16, wherein the orthodontic prescription-defining device is a first orthodontic prescription-defining device that defines a first preselected orientation between the plurality of archwire slots and the plurality of intra-oral reference points, and further wherein the method includes repeating at least the operatively contacting and the urging with a second orthodontic prescription-defining device, which is different from the first orthodontic prescription-defining device, to define a second preselected orientation between the plurality of archwire slots and the plurality of intra-oral reference points, wherein the second preselected orientation is different from the first preselected orientation.

C18. The method of any of paragraphs C1-C17, wherein the plurality of orthodontic brackets is a first plurality of orthodontic brackets, wherein the orthodontic prescription-defining device is a first orthodontic prescription-defining device, and further wherein the method includes repeating at least the unlocking, the operatively contacting, the urging, and the locking with a second orthodontic prescription-defining device to urge a second plurality of orthodontic brackets to a respective preselected orientation, wherein the second plurality of orthodontic brackets is different from the first plurality of orthodontic brackets.

C19. The method of any of paragraphs C1-C18, wherein the method further includes forming the orthodontic prescription-defining device based, at least in part, on at least one of:
  (i) a three-dimensional model of the patient's mouth;
  (ii) a three-dimensional model of a predetermined intra-oral reference point associated with each of the plurality of contacting structures;
  (iii) a three-dimensional model of the plurality of orthodontic brackets while each of the plurality of orthodontic brackets is operatively affixed to a corresponding tooth;
  (iv) a three-dimensional model of the plurality of archwire slots;
  (v) an initial occlusion of at least one tooth;
  (vi) a current occlusion of at least one tooth;
  (vii) a desired occlusion of at least one tooth; and
  (viii) a location of each of the plurality of orthodontic brackets on the corresponding tooth.

C20. The method of any of paragraphs C1-C19, wherein the method further includes generating a/the three-dimensional model of the patient's mouth, and optionally wherein the method includes forming the orthodontic prescription-defining device based, at least in part, on the three-dimensional model of the patient's mouth.

C21. The method of any of paragraphs C1-C20, wherein the orthodontic prescription-defining device defines the preselected orientation prior to performing the method, and optionally wherein the preselected orientation is based, at least in part, on at least one of:
  (i) a/the three-dimensional model of the patient's mouth;
  (ii) a/the three-dimensional model of the predetermined intra-oral reference point associated with each of the plurality of contacting structures;
  (iii) a/the three-dimensional model of the plurality of orthodontic brackets while each of the plurality of orthodontic brackets is operatively affixed to a/the corresponding tooth;
  (iv) a/the three-dimensional model of the plurality of archwire slots;
  (v) an/the initial occlusion of at least one tooth;
  (vi) a/the current occlusion of at least one tooth;
  (vii) a/the desired occlusion of at least one tooth; and
  (viii) a/the location of each of the plurality of orthodontic brackets on the corresponding tooth.

INDUSTRIAL APPLICABILITY

The systems and methods disclosed herein are applicable to the dental and orthodontics industries.

It is believed that the disclosure set forth above encompasses multiple distinct inventions with independent utility. While each of these inventions has been disclosed in its preferred form, the specific embodiments thereof as disclosed and illustrated herein are not to be considered in a limiting sense as numerous variations are possible. The subject matter of the inventions includes all novel and non-obvious combinations and subcombinations of the various elements, features, functions and/or properties disclosed herein. Similarly, where the claims recite "a" or "a first" element or the equivalent thereof, such claims should be understood to include incorporation of one or more such elements, neither requiring nor excluding two or more such elements.

It is believed that the following claims particularly point out certain combinations and subcombinations that are directed to one of the disclosed inventions and are novel and non-obvious. Inventions embodied in other combinations and subcombinations of features, functions, elements and/or properties may be claimed through amendment of the present claims or presentation of new claims in this or a related application. Such amended or new claims, whether they are directed to a different invention or directed to the same invention, whether different, broader, narrower, or equal in scope to the original claims, are also regarded as included within the subject matter of the inventions of the present disclosure.

The invention claimed is:

1. An orthodontic prescription-defining device configured to concurrently adjust an orientation of a plurality of archwire slots of a plurality of orthodontic brackets that are operatively affixed to a corresponding plurality of teeth within a patient's mouth; wherein each of the plurality of orthodontic brackets includes a base that is operatively affixed to the corresponding tooth and a body that is configured to be selectively repositioned relative to the base while the base is operatively affixed to the corresponding tooth; wherein the body defines an archwire slot of the plurality of archwire slots that is configured to receive an archwire; wherein each of the plurality of orthodontic brackets defines a locked configuration in which an orientation of the archwire slot relative to the base is at least substantially fixed; and wherein each of the plurality of orthodontic brackets further defines an unlocked configuration that permits the orientation of the archwire slot relative to the base to be varied via relative motion between the body and the base; the device comprising:
  a plurality of contacting structures, wherein each of the plurality of contacting structures is configured to operatively contact a respective predetermined intra-oral reference point of a plurality of intra-oral reference points within the patient's mouth to define a predetermined orientation of the orthodontic prescription-defining device relative to the plurality of intra-oral reference points and relative to the bases of the plurality of orthodontic brackets that are operatively affixed to the corresponding plurality of teeth; and
  a plurality of prescription-defining engagement structures connected to the plurality of contacting structures;
  wherein each of the plurality of prescription-defining engagement structures is configured to urge a respective archwire slot of a respective orthodontic bracket of the plurality of orthodontic brackets to move relative to a respective base of the respective orthodontic bracket to transition the respective archwire slot from a respective first orientation relative to the respective base of the respective orthodontic bracket to a respective preselected orientation relative to the respective base of the respective orthodontic bracket when the respective orthodontic bracket is in the unlocked configuration.

2. The device of claim 1, wherein each of the plurality of prescription-defining engagement structures is configured to operatively contact a respective body of a respective orthodontic bracket of the plurality of orthodontic brackets to urge the respective body of the respective orthodontic bracket to move relative to a respective base of the respective orthodontic bracket to transition a respective archwire slot of the respective orthodontic bracket from a respective first orientation relative to the respective base of the respective orthodontic bracket to a respective preselected orientation relative to the respective base of the respective orthodontic bracket when the respective orthodontic bracket is in the unlocked configuration.

3. The device of claim 1, wherein each of the plurality of prescription-defining engagement structures is configured to be received within a respective archwire slot of a respective orthodontic bracket of the plurality of orthodontic brackets to urge a respective body of the respective orthodontic bracket to move relative to a respective base of the respective orthodontic bracket to transition the respective archwire slot from a respective first orientation relative to the respective base of the respective orthodontic bracket to a respective preselected orientation relative to the respective base of the respective orthodontic bracket when the respective orthodontic bracket is in the unlocked configuration.

4. The device of claim 1, wherein each of the plurality of prescription-defining engagement structures is configured to operatively contact a portion of the archwire proximate a respective archwire slot of a respective orthodontic bracket to urge a respective body of the respective orthodontic bracket to move relative to a respective base of the respective orthodontic bracket to transition the respective archwire slot from a respective first orientation relative to the respective base of the respective orthodontic bracket to a respective preselected orientation relative to the respective base of the respective orthodontic bracket when the respective orthodontic bracket is in the unlocked configuration.

5. The device of claim 1, wherein each of the plurality of prescription-defining engagement structures is configured to urge a respective body of a respective orthodontic bracket to move relative to a respective base of the respective orthodontic bracket to transition a respective archwire slot of the respective orthodontic bracket from a respective first orientation relative to the respective base of the respective orthodontic bracket to a respective preselected orientation relative to the respective base of the respective orthodontic bracket when the respective orthodontic bracket is in the unlocked configuration and when the archwire is received within the respective archwire slot.

6. The device of claim 1, wherein each of the plurality of prescription-defining engagement structures is configured to urge a respective body of a respective orthodontic bracket to move relative to a respective base of the respective orthodontic bracket to transition a respective archwire slot of the respective orthodontic bracket from a respective first orientation relative to the respective base of the respective orthodontic bracket to a respective preselected orientation relative to the respective base of the respective orthodontic bracket when the respective orthodontic bracket is in the unlocked configuration and when the archwire is removed from the respective archwire slot.

7. The device of claim 1, wherein the orthodontic prescription-defining device is a monolithic orthodontic prescription-defining device that defines the plurality of contacting structures and the plurality of prescription-defining engagement structures.

8. The device of claim 1, wherein the orthodontic prescription-defining device is a composite structure that includes a contacting body that defines the plurality of contacting structures and is operatively attached to the plurality of prescription-defining engagement structures.

9. The device of claim 8, wherein each of the plurality of prescription-defining engagement structures is configured to be selectively transitioned between a disengaged configuration and an engaged configuration while the plurality of contacting structures operatively contacts the corresponding plurality of respective intra-oral reference points; wherein, when a respective prescription-defming engagement structure of the plurality of prescription-defining engagement structures is in the disengaged configuration, the respective prescription-defining engagement structure is separated from a respective orthodontic bracket of the plurality of orthodontic brackets, and wherein, when the respective prescription-defining engagement structure of the plurality of prescription-defining engagement structures is in the engaged configuration, the respective prescription-defining engagement structure is configured to urge a respective body of the respective orthodontic bracket to move relative to a respective base of the respective orthodontic bracket to transition a respective archwire slot of the respective orthodontic bracket from a respective first orientation relative to the respective base of the respective orthodontic bracket to a respective preselected orientation relative to the respective base of the respective orthodontic bracket when the respective orthodontic bracket is in the unlocked configuration.

10. An orthodontic appliance system, comprising:
  the orthodontic prescription-defining device of claim 1; and
  the plurality of orthodontic brackets.

11. The system of claim 10, wherein the orthodontic prescription-defining device is a first orthodontic prescription-defining device, wherein the system includes a plurality of orthodontic prescription-defining devices, and further wherein each of the plurality of orthodontic prescription-defining devices defines a respective preselected orientation of each of the respective archwire slots of the plurality of orthodontic brackets relative to each of the respective bases of the plurality of orthodontic brackets.

12. The system of claim 11, wherein the plurality of orthodontic prescription-defining devices defines a progressive prescription sequence that is configured to apply a sequence of prescriptive forces to a plurality of teeth to progressively move the plurality of teeth from an initial occlusion to a desired occlusion.

13. The system of claim 10, wherein the system includes a plurality of orthodontic prescription-defining devices, wherein each of the plurality of orthodontic prescription-defining devices is configured to urge a respective subset of respective bodies of a respective subset of orthodontic brackets of the plurality of orthodontic brackets to move relative to a respective subset of respective bases of the respective subset of orthodontic brackets to transition a respective subset of the plurality of archwire slots from corresponding respective first orientations relative to the respective subset of the respective bases of the respective subset of orthodontic brackets to corresponding respective preselected orientations relative to the respective subset of the respective bases of the respective subset of orthodontic brackets when each of the respective subsets of orthodontic brackets are in the unlocked configuration.

14. The system of claim 10, wherein the system further includes an orthodontic prescription-defining device fabrication assembly that is configured to be utilized by an orthodontist to create the orthodontic prescription-defining device.

15. A method of adjusting an orientation of a plurality of archwire slots of a plurality of orthodontic brackets affixed to a corresponding plurality of teeth within a patient's mouth to define a prescription of the plurality of orthodontic brackets, wherein each of the plurality of orthodontic brackets includes a base that is operatively affixed to the corresponding tooth and a body that is configured to be selectively repositioned relative to the base while the base is operatively affixed to the corresponding tooth; wherein the body defines an archwire slot of the plurality of archwire slots that is configured to receive an archwire, and further wherein each of the plurality of orthodontic brackets defines a locked configuration in which an orientation of the archwire slot relative to the base is at least substantially fixed, and an unlocked configuration that permits the orientation of the archwire slot relative to the base to be varied via relative motion between the body and the base, the method comprising:

unlocking each of the plurality of orthodontic brackets by transitioning each of the plurality of orthodontic brackets to a respective unlocked configuration while the bases of each of the plurality of orthodontic bases remain operatively affixed to the corresponding teeth of the plurality of teeth in the patient's mouth;

operatively contacting a plurality of contacting structures of an orthodontic prescription-defining device with a plurality of intra-oral reference points within the patient's mouth while the bases of each of the plurality of orthodontic brackets remain operatively affixed to the corresponding teeth of the plurality of teeth in the patient's mouth to define a predetermined orientation of the orthodontic prescription-defining device relative to the plurality of intra-oral reference points and relative to the bases of the plurality of orthodontic brackets that are operatively affixed to the corresponding plurality of teeth;

concurrently with the operatively contacting, urging, with each of a plurality of prescription-defining engagement structures of the orthodontic prescription-defining device, a respective body of a respective orthodontic bracket to move relative to a respective base of the respective orthodontic bracket to transition a respective archwire slot of the respective orthodontic bracket from a respective first orientation relative to the plurality of intra-oral reference points to a respective preselected orientation relative to the plurality of intra-oral reference points; and locking each of the plurality of orthodontic brackets by transitioning each of the plurality of orthodontic brackets to a respective locked configuration.

16. The method of claim 15, wherein the urging includes directly and operatively engaging at least one of the plurality of prescription-defining engagement structures with a corresponding orthodontic bracket of the plurality of orthodontic brackets.

17. The method of claim 15, wherein the urging includes directly and operatively engaging the archwire to indirectly urge each of the plurality of archwire slots to the respective preselected orientation.

18. The method of claim 17, wherein the directly and operatively engaging the archwire includes at least one of twisting the archwire, bending the archwire, and deforming the archwire.

19. The method of claim 15, wherein, prior to the operatively contacting, the method further includes removing the archwire from the plurality of archwire slots, and further wherein, subsequent to the locking, the method further includes locating the archwire within the plurality of archwire slots.

20. The method of claim 15, wherein the method includes performing at least the operatively contacting and the urging while the archwire extends within the plurality of archwire slots.

21. The method of claim 15, wherein, subsequent to the locking, the method further includes separating the orthodontic prescription-defining device from the plurality of intra-oral reference points and from the plurality of orthodontic brackets.

22. The method of claim 15, wherein the orthodontic prescription-defining device is a first orthodontic prescription-defining device that defines a first preselected orientation between the plurality of archwire slots and the plurality of intra-oral reference points, and further wherein the method includes repeating at least the operatively contacting and the urging with a second orthodontic prescription-defining device, which is different from the first orthodontic prescription-defining device, to define a second preselected orientation between the plurality of archwire slots and the plurality of intra-oral reference points, wherein the second preselected orientation is different from the first preselected orientation.

23. The method of claim 15, wherein the plurality of orthodontic brackets is a first plurality of orthodontic brackets, wherein the orthodontic prescription-defining device is a first orthodontic prescription-defining device, and further wherein the method includes repeating at least the unlocking, the operatively contacting, the urging, and the locking with a second orthodontic prescription-defining device to urge a second plurality of orthodontic brackets to a respective preselected orientation, wherein the second plurality of orthodontic brackets is different from the first plurality of orthodontic brackets.

24. A method of adjusting an orientation of a plurality of archwire slots of a plurality of orthodontic brackets to define a prescription of the plurality of orthodontic brackets while each of the plurality of orthodontic brackets is operatively affixed to a corresponding tooth within a patient's mouth, wherein each of the plurality of orthodontic brackets includes a base configured to be operatively affixed to the corresponding tooth and a body that is configured to be selectively repositioned relative to the base and that defines an archwire slot of the plurality of archwire slots that is configured to receive an archwire, and further wherein each of the plurality of orthodontic brackets defines a locked configuration in which an orientation of the archwire slot relative to the base is at least substantially fixed, and an unlocked configuration that permits the orientation of the archwire slot relative to the base to be varied via relative motion between the body and the base, the method comprising:

unlocking each of the plurality of orthodontic brackets by transitioning each of the plurality of orthodontic brackets to a respective unlocked configuration;

operatively contacting a plurality of contacting structures of an orthodontic prescription-defining device with a plurality of intra-oral reference points within the patient's mouth to define a predetermined orientation of the orthodontic prescription-defining device within the patient's mouth;

concurrently with the operatively contacting, urging, with a plurality of prescription-defining engagement structures of the orthodontic prescription-defining device, each of the plurality of archwire slots to a respective preselected orientation relative to the plurality of intra-oral reference points; and locking each of the plurality of orthodontic brackets by transitioning each of the plurality of orthodontic brackets to a respective locked configuration;

wherein the urging includes directly and operatively engaging the archwire to indirectly urge each of the plurality of archwire slots to the respective preselected orientation.

25. The method of claim 24, wherein the directly and operatively engaging the archwire includes at least one of twisting the archwire, bending the archwire, and deforming the archwire.

* * * * *

UNITED STATES PATENT AND TRADEMARK OFFICE
CERTIFICATE OF CORRECTION

PATENT NO. : 9,918,807 B2
APPLICATION NO. : 14/694308
DATED : March 20, 2018
INVENTOR(S) : Christopher C. Cosse It is certified that error appears in the above-identified patent and that said Letters Patent is hereby corrected as shown below:

In the Claims

Column 28, Line 64, before "a locked configuration" please delete "defmes" and insert --defines--.

Signed and Sealed this
Eighth Day of May, 2018

Andrei Iancu
*Director of the United States Patent and Trademark Office*